United States Patent
Adam

(10) Patent No.: US 9,955,974 B2
(45) Date of Patent: May 1, 2018

(54) INVERTED DIVERTICULUM TREATMENT DEVICES

(71) Applicant: Empire Technology Development LLC, Wilmington, DE (US)

(72) Inventor: Quentin Arthur Carl Adam, New South Wales (AU)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 589 days.

(21) Appl. No.: 14/394,408

(22) PCT Filed: Mar. 10, 2014

(86) PCT No.: PCT/US2014/022470
§ 371 (c)(1),
(2) Date: Oct. 14, 2014

(87) PCT Pub. No.: WO2015/137909
PCT Pub. Date: Sep. 17, 2015

(65) Prior Publication Data
US 2016/0213374 A1 Jul. 28, 2016

(51) Int. Cl.
*A61B 17/10* (2006.01)
*A61B 17/12* (2006.01)
(Continued)

(52) U.S. Cl.
CPC .... *A61B 17/12013* (2013.01); *A61B 17/1285* (2013.01); *A61B 90/361* (2016.02);
(Continued)

(58) Field of Classification Search
CPC .......... A61B 17/12013; A61B 17/1285; A61B 2017/00818; A61B 2018/00482; A61B 2018/00494
See application file for complete search history.

(56) References Cited

U.S. PATENT DOCUMENTS 4,470,415 A 9/1984 Wozniak
5,100,419 A 3/1992 Ehlers
(Continued)

FOREIGN PATENT DOCUMENTS

EP 1 026 996 10/2007

OTHER PUBLICATIONS

"Endoscopy," accessed at http://web.archive.org/web/20130907173659/http://en.wikipedia.org/wiki/Endoscopy, last modified on Sep. 2, 2013, pp. 1-10.
(Continued)

*Primary Examiner* — Ashley Fishback
(74) *Attorney, Agent, or Firm* — Maschoff Brennan

(57) ABSTRACT

A device for treating a diverticulum includes a containment device and a bushing. The containment device includes an elongate conduit. The bushing is in the conduit of the containment device. The bushing includes a heat-shrink material. The bushing has a first tubular shape including a first open end and a second open end. At least a portion of the diverticulum in an inverted state is positionable into the first open end. The bushing is configured to transform from the first tubular shape toward a second shape upon heating the heat-shrink material. The second shape includes at least a portion of the bushing radially inward relative to the first tubular shape. The bushing in the second shape is configured to hold the diverticulum in a radially compressed inverted state.

18 Claims, 17 Drawing Sheets

(51) Int. Cl.
*A61B 17/128* (2006.01)
*A61B 17/00* (2006.01)
*A61B 90/00* (2016.01)

(52) U.S. Cl.
CPC ............... *A61B 2017/00292* (2013.01); *A61B 2017/00415* (2013.01); *A61B 2017/00818* (2013.01); *A61B 2017/00867* (2013.01); *A61B 2017/00955* (2013.01)

(56) References Cited

U.S. PATENT DOCUMENTS

| | | |
|---|---|---|
| 5,403,331 A | 4/1995 | Chesterfield et al. |
| 5,507,797 A | 4/1996 | Suzuki et al. |
| 6,248,118 B1 | 6/2001 | Tanner et al. |
| 7,278,994 B2 | 10/2007 | Goble |
| 7,331,969 B1 | 2/2008 | Inganas et al. |
| 8,062,308 B2 | 11/2011 | Noda et al. |
| 2002/0052660 A1 | 5/2002 | Greenhalgh |
| 2006/0235077 A1 | 10/2006 | Taheri |
| 2007/0015965 A1 | 1/2007 | Cox et al. |
| 2007/0179598 A1 | 8/2007 | Duerig |
| 2007/0260112 A1 | 11/2007 | Rahmani |
| 2007/0270886 A1 | 11/2007 | McGuckin, Jr. et al. |
| 2008/0249506 A1 | 10/2008 | Neustaedter et al. |
| 2008/0262514 A1 | 10/2008 | Gasche et al. |
| 2009/0105728 A1 | 4/2009 | Noda et al. |
| 2009/0125037 A1 | 5/2009 | Goto |
| 2009/0192510 A1 | 7/2009 | Bahney |
| 2010/0198016 A1 | 8/2010 | Tilson et al. |
| 2010/0331625 A1 | 12/2010 | Rosemurgy et al. |
| 2011/0166563 A1 | 7/2011 | Cheng et al. |
| 2011/0277777 A1 | 11/2011 | Alexander et al. |
| 2011/0277778 A1 | 11/2011 | Alexander et al. |
| 2012/0053577 A1 | 3/2012 | Lee et al. |
| 2012/0265000 A1 | 10/2012 | Ivkov et al. |
| 2013/0197547 A1* | 8/2013 | Fukuoka ............... A61B 17/122 606/157 |

OTHER PUBLICATIONS

"Heat-shrink tubing," accessed at http://web.archive.org/web/20140211022317/http://en.wikipedia.org/wiki/Heat-shrink_tubing, last modified on Nov. 27, 2013, pp. 1-5.

"Shrink wrap," accessed at http://web.archive.org/web/20140219171815/http://en.wikipedia.org/wiki/Shrink_wrap, last modified on Jan. 28, 2014, pp. 1-9.

Del Genio et al., "What are the indications for endoscopic methods of treatment ?" accessed at http://web.archive.org/web/20130702151414/http://www.hon.ch/OESO/books/Vol_4_Prim_Motility/Articles/ART312.HTML, published on May 1991, pp. 1-2.

Kelsey, P.B., "Colon-Diverticular Bleeding Treated with Banding Therapy, Example 2," Harvard Medical School, Massachusetts General Hospital, accessed at http://web.archive.org/web/20120618213817/http://daveproject.org/colon-diverticular-bleeding-treated-with-banding-therapy-example-2/2003-11-25/, posted on Nov. 25, 2003, pp. 1-2.

International Search Report and Written Opinion issued in Patent Cooperation Treaty Application No. PCT/US14/22470, dated Aug. 25, 2014, in 18 pages.

* cited by examiner

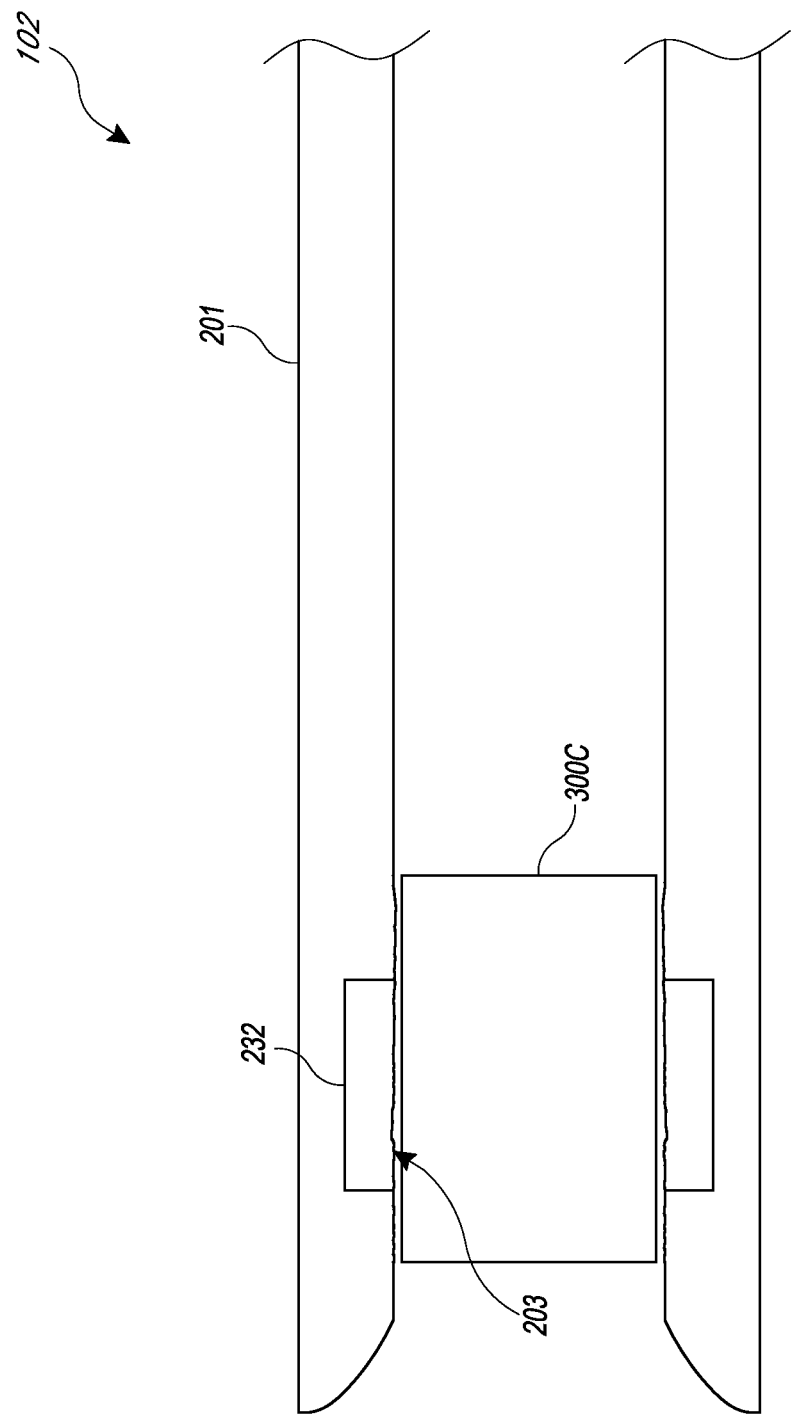

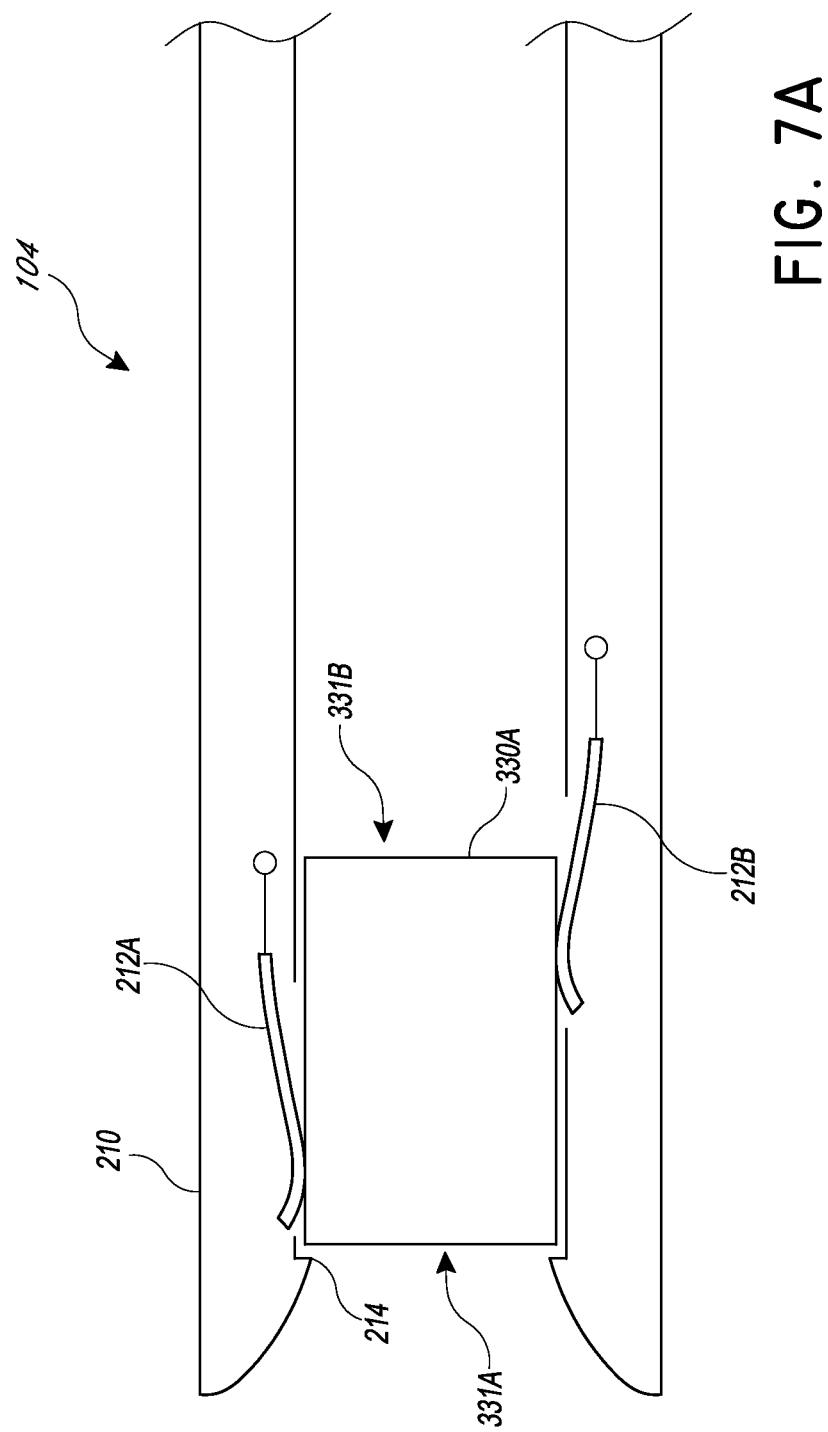

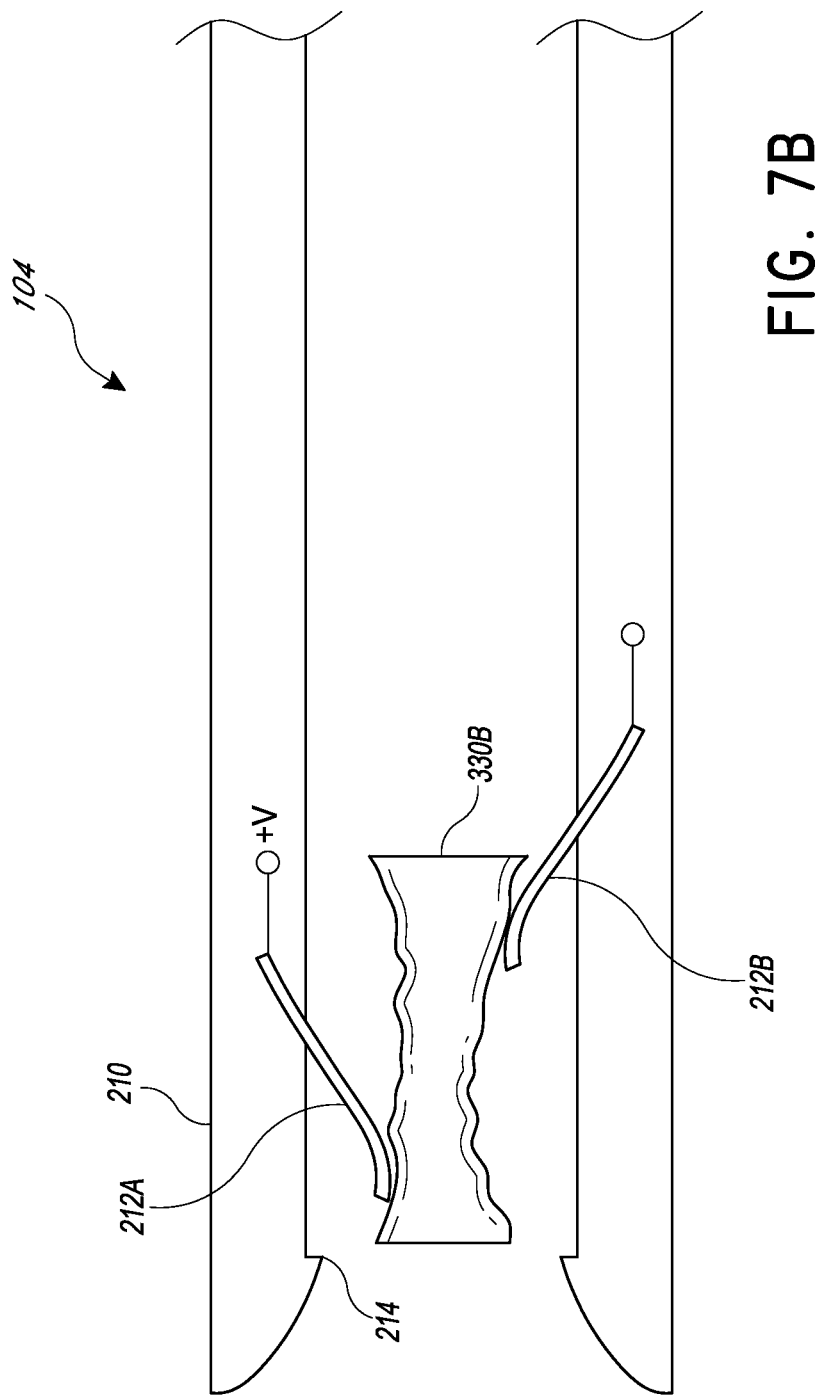

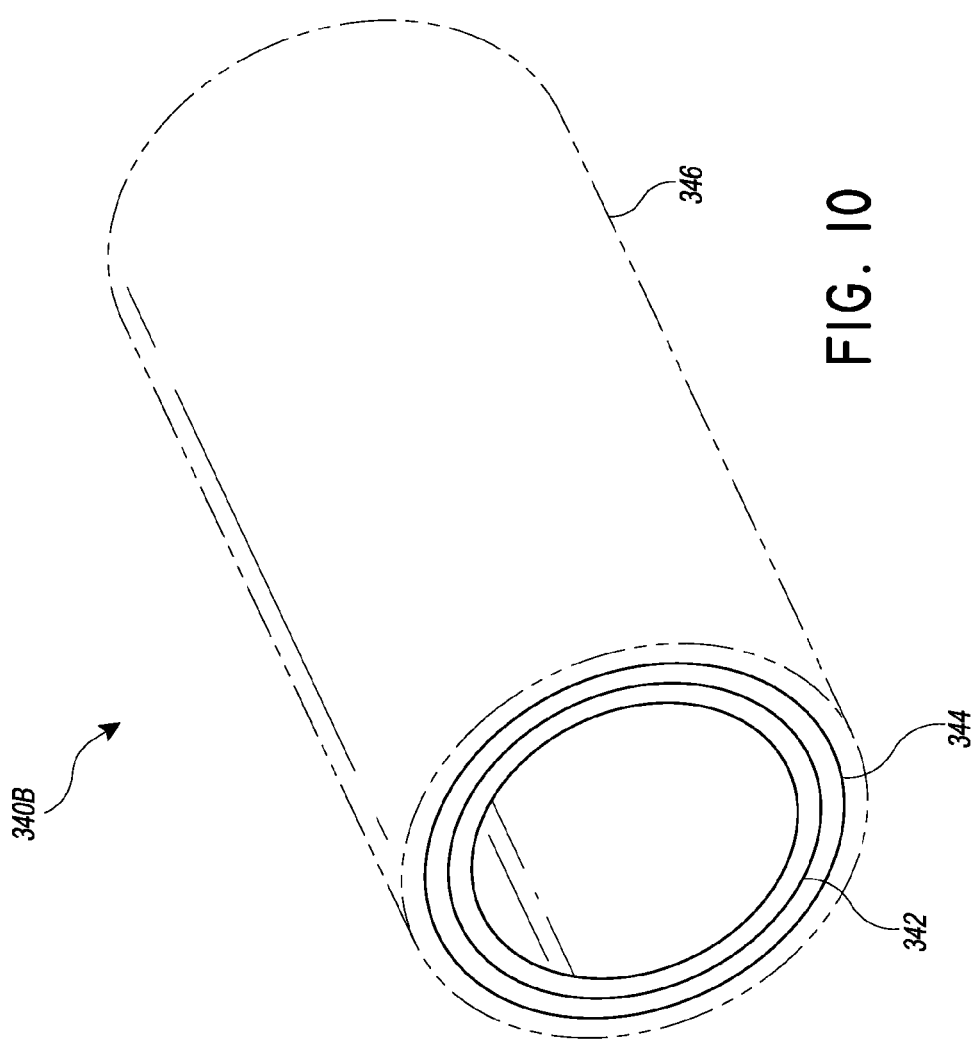

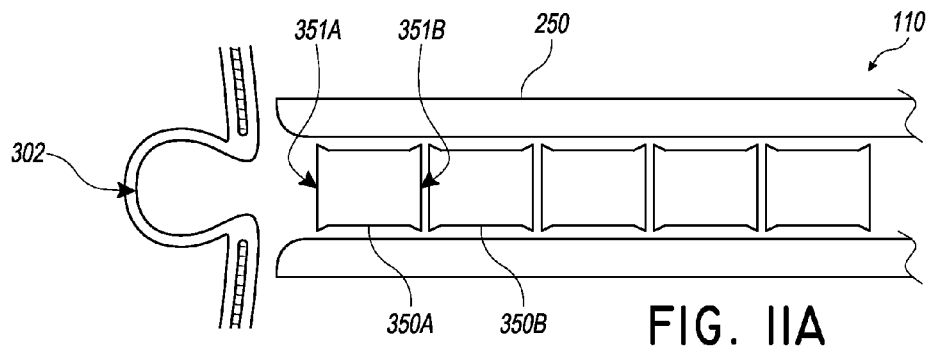
FIG. IIA
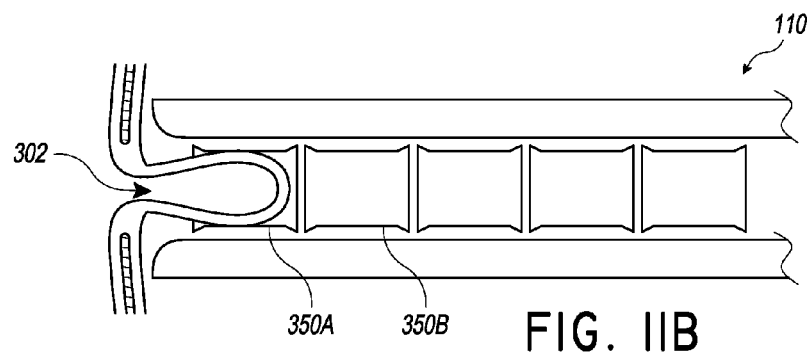
FIG. IIB
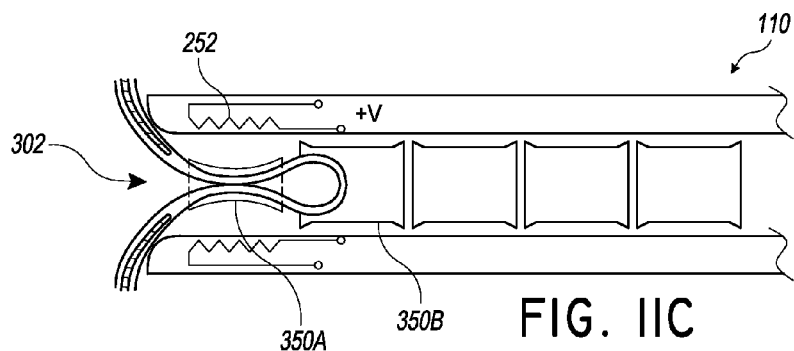
FIG. IIC
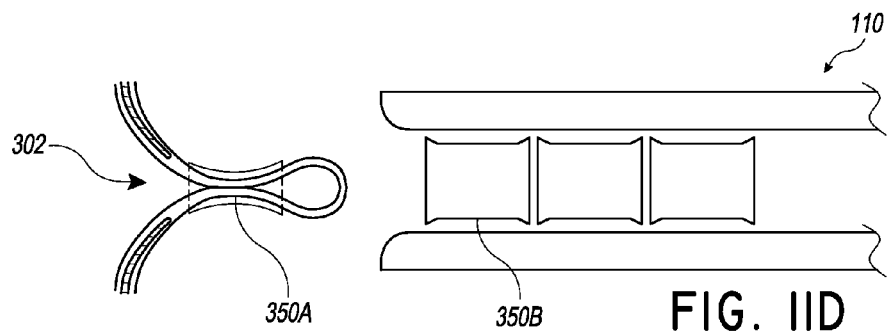
FIG. IID

INVERTED DIVERTICULUM TREATMENT DEVICES

CROSS-REFERENCE TO RELATED APPLICATION

This application is a U.S. National Stage filing under 35 U.S.C. § 371 of International Application No. PCT/2014/022470, filed on Mar. 10, 2014, which is hereby incorporated by reference in its entirety.

BACKGROUND

An outpouching of the colon or other body lumen, called a diverticulum, can become the site for inflammation known as diverticulitis, microperforation and/or bleeding. Current treatments may involve the surgical removal of segments of the body lumen. For extreme cases of diverticulitis, treatment can involve colon resection and placement of a colostomy. This approach results in significant healthcare costs and substantial pain for patients.

SUMMARY

In some implementations, a method of treating a diverticulum of a body lumen can include positioning the diverticulum in an inverted state at least partially into a first open end of a bushing in an elongate conduit of a containment device. The bushing includes a heat-shrink material. The method can further include transforming the bushing from a first tubular shape including the first open end and a second open end toward a second shape. Transforming the bushing includes heating the heat-shrink material. The second shape includes at least a portion of the bushing radially inward relative to the first tubular shape. After transforming the bushing, the bushing in the second state holds the diverticulum in a radially compressed inverted state.

The containment device can include a distal end including a resistive heating element, and heating the heat-shrink material can include applying current to the resistive heating element. The containment device can include a distal end including flexible electrical contacts, and heating the heat-shrink material can include applying current to the flexible electrical contacts. The containment device can include a distal end including a solenoid, and heating the heat-shrink material can include applying current to the solenoid. After transforming the bushing, at least part of the inverted diverticulum can extend out of the second open end of the bushing. The method can further include cauterizing a mouth of the inverted diverticulum. The method can further include applying pressure to the diverticulum sufficient to cause at least a portion of the diverticulum to invert. Applying the pressure can include applying negative pressure within the conduit of the containment device. The method can further include imaging the bushing during transforming the bushing. The body lumen can be a colon. A colonoscope can include the containment device, and the method can further include advancing the colonoscope proximate to the diverticulum. The method can further include deploying the bushing out of the conduit of the containment device. Deploying the bushing out of the conduit of the containment device can include deploying the bushing out of a longitudinal end of the containment device. Deploying the bushing out of the conduit of the containment device can include deploying the bushing out of a side of the containment device.

The method can further include, after transforming the bushing and without withdrawing the containment device from the body lumen, distally advancing a second bushing in the conduit of the containment device. The second bushing includes a heat-shrink material, a first open end, and a second open end. The method can further include positioning a second diverticulum in an inverted state at least partially into the first open end of the second bushing in the elongate conduit of the containment device and transforming the second bushing from a first tubular shape including the first open end and the second open end toward a second shape. Transforming the second bushing includes heating the heat-shrink material. The second shape includes at least a portion of the second bushing radially inward relative to the first tubular shape. After transforming the second bushing, the second bushing in the second state holds the second diverticulum in a radially compressed inverted state.

In some implementations, a device for treating a diverticulum can include a containment device and a bushing. The containment device includes an elongate conduit. The bushing is in the conduit of the containment device. The bushing includes a heat-shrink material. The bushing has a first tubular shape including a first open end and a second open end. At least a portion of the diverticulum in an inverted state is positionable into the first open end. The bushing is configured to transform from the first tubular shape toward a second shape upon heating the heat-shrink material. The second shape includes at least a portion of the bushing radially inward relative to the first tubular shape. The bushing in the second shape is configured to hold the diverticulum in a radially compressed inverted state.

The heat-shrink material can include at least one of nylon, thermoplastic such as polyolefin, fluoropolymer, fluorinated ethylene propylene (FEP), polytetrafluoroethylene (PTFE), polyvinylidene fluoride (PVDF), polyvinyl chloride (PVC), polycholorprene, and silicone elastomer. The containment device can include a distal end including a heating element. The heating element can include a resistive heating element. The resistive heating element can include a tungsten wire. The resistive heating element can include a ceramic block. The heating element can have a longitudinal length less than a longitudinal length of the bushing within the elongate conduit. The bushing can include an intermediate portion between the first open end and the second open end, and the heating element can be configured to radially irradiate the intermediate portion. The heating element can be configured to cauterize a mouth of the diverticulum. The bushing can include a first electrically conductive track, a second electrically conductive track, and an ohmic resistor between the first electrically conductive track and the second electrically conductive track. The containment device can include a distal end including a first contact configured to conduct electrical current to the first electrically conductive track and a second contact configured to conduct electrical current to the second electrically conductive track. At least one of the first contact and the second contact can include a spring contact biased radially inwardly. The bushing can include a foil layer external to the heat-shrink material. The bushing can include a polymer corrosion barrier external to the foil layer. The containment device can include a distal end including a solenoid. The containment device can be configured to invert at least a portion of the diverticulum upon application of negative pressure to the elongate conduit of the containment device. At least one of the first open end of the bushing and the second open end of the bushing can include a flared end. The first open end of the bushing can include a trumpeted end. The first open end of the bushing can include a plurality of longitudinal slots. The first open end of the bushing can include a ring not including the heat-shrink material. The bushing can include a longitudinal slot between the first open end and the second open end. The longitudinal slot is configured such that the bushing folds upon itself upon heating the heat-shrink material. The bushing can include a roughened inner surface configured to frictionally engage the inverted diverticulum. A ratio of a transverse diameter of the bushing to a longitudinal length of the bushing can be between about 0.5:1 and about 2:1. The device can further include a plurality of said bushings arranged longitudinally in the elongate conduit of the containment device. The device can further include a pusher configured to longitudinally distally advance the plurality of bushings. The containment device can include an imaging system configured to monitor transforming the bushing from the first tubular state toward the second state. The containment device can include a radially inward protrusion distal to the bushing. The radially inward protrusion is configured to inhibit the bushing from exiting the containment device in the first tubular shape. The containment device can include an inner surface configured to frictionally inhibit the bushing from exiting the containment device in the first tubular shape. The containment device can include a thermally insulated endoscope head configured to inhibit heating of biologic tissue not within the elongate conduit. A colonoscope can include the containment device.

In some implementations, a bushing for treating a diverticulum can include a first open end, a second open end, a tubular body between the first open end and the second open end, a first electrically conductive track proximate to the first open end, a second electrically conductive track proximate to the second open end, and an ohmic resistor between the first electrically conductive track and the second electrically conductive track. The tubular body includes heat-shrink material configured to compress radially inwardly upon application of an electric current between the first electrically conductive track and the second electrically conductive track.

The heat-shrink material can include at least one of nylon, thermoplastic such as polyolefin, fluoropolymer, fluorinated ethylene propylene (FEP), polytetrafluoroethylene (PTFE), polyvinylidene fluoride (PVDF), polyvinyl chloride (PVC), polycholorprene, and silicone elastomer. At least one of the first open end and the second open end can include a flared end. The first open end can include a trumpeted end. The first open end can include a plurality of longitudinal slots. The tubular body can include a longitudinal slot extending from the first open end to the second open end. The longitudinal slot is configured such that the bushing folds upon itself upon heating the heat-shrink material. The tubular body can include a plurality of transverse slots between the first open end and the second open end. The plurality of transverse slots is configured to increase longitudinal flexibility of the bushing. The tubular body can further include a spiral cut between the first open end and the second open end. The spiral cut is configured to increase longitudinal flexibility of the bushing.

In some implementations, a bushing for treating a diverticulum can include a first open end, a second open end, and a tubular body between the first open end and the second open end. The tubular body includes heat-shrink material and a foil layer external to the heat-shrink material. The heat-shrink material is configured to compress radially inwardly upon application of an inductive current to the foil layer.

The tubular body can further include a polymer barrier external to the foil layer. The heat-shrink material can include at least one of nylon, thermoplastic such as polyolefin, fluoropolymer, fluorinated ethylene propylene (FEP), polytetrafluoroethylene (PTFE), polyvinylidene fluoride (PVDF), polyvinyl chloride (PVC), polycholorprene, and silicone elastomer. At least one of the first open end and the second open end can include a flared end. The first open end can include a trumpeted end. The first open end can include a plurality of longitudinal slots. The tubular body can include a longitudinal slot extending from the first open end to the second open end. The longitudinal slot is configured such that the bushing folds upon itself upon heating the heat-shrink material. The tubular body can include a plurality of transverse slots between the first open end and the second open end. The plurality of transverse slots is configured to increase longitudinal flexibility of the bushing. The tubular body can further include a spiral cut between the first open end and the second open end. The spiral cut is configured to increase longitudinal flexibility of the bushing.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through use of the accompanying drawings.

FIG. 4C is a partial cross-sectional side view of another example embodiment of a device including a containment device and a bushing.

FIGS. 7A and 7B are partial cross-sectional side views of an example embodiment of a device including a containment device and a bushing.

FIG. 10 is a perspective view of an example embodiment of a bushing.

FIGS. 11A-11D illustrate an example embodiment of a method of treating a diverticulum using a device including a containment device and a bushing.

DETAILED DESCRIPTION

Figure 1:
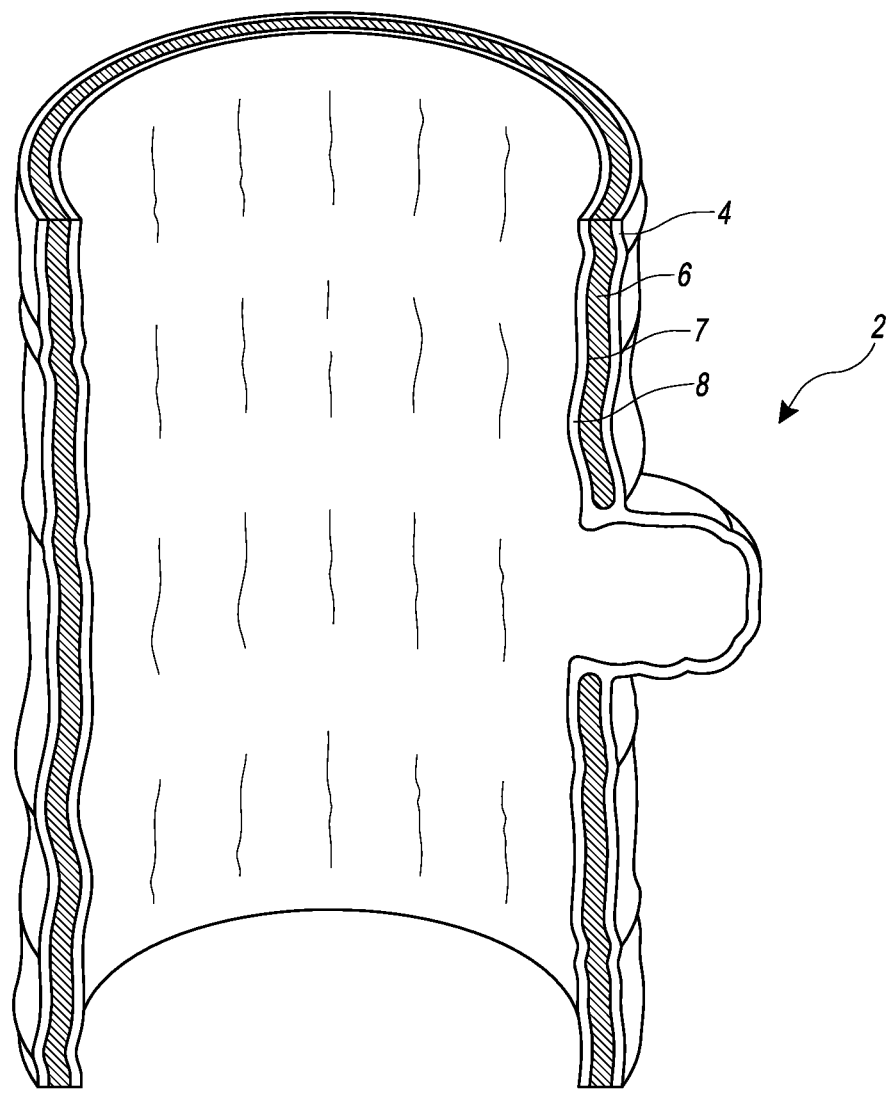
FIG. 1 is a cross-sectional view of a diverticulum of the sigmoid colon showing the structural makeup.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated and made part of this disclosure.

Diverticula of the lower colon can become the site for microperforation and inflammation called diverticulitis and/or bleeding. A device disclosed herein can be used to invert, close, and remove diverticula of the colon, sparing the patient of colon resection surgery. Current treatment strategies for treating diverticula may involve the surgical removal of large segments of the colon, and in extreme cases, the placement of a colostomy. An alternative treatment strategy is provided that can be performed during routine colon examinations, where a colonoscope is used to identify a diverticulum, and also deliver the tools to the site for inverting and ligating the diverticulum. The working channel of the colonoscope may be used to invert the diverticulum and to deploy a bushing including a shape-memory material, which can hold the diverticulum in a radially compressed inverted state. The device may be configured to fit within the working channel of the colonoscope, thereby allowing the physician/operator to identify an individual diverticulum, invert it, and tie it off with a bushing proximate to the base of the diverticulum. Means can be provided to verify that the full diverticulum is inverted and that the base is sealed in such a manner as to reduce the opening in the muscular layer of the colon wall, to reduce or minimize circulation of blood into the tissue.

In conventional colonoscopy procedures, a gastroenterologist advances a colonoscope completely to the patient's appendix while inflating the colon with air. Visual examination is preformed while retracting the colonoscope. Diverticula are generally easy to see and diagnose visually. If treatment of the diverticulum is deemed warranted by the physician, the whole colonoscope must be removed (4-5 ft. long) in order to slide an overtube assembly onto the colonoscope. Then the colonoscope is reinserted while looking to find the diverticulum. This is a tedious, time-consuming, and potentially dangerous procedure. In contrast, according to embodiments disclosed herein, once a diverticulum is detected, the physician can keep the colonoscope in the colon and focused on the diverticulum, and advance the disclosed device down the working channel of the colonoscope in order to treat the diverticulum quickly. Once the diverticulum is inverted and tied off, further examination of the colon can continue and other treatments, such as polyp removal, can continue also using the working channel. The substantial burden of removing the colonoscope from the patient, sliding an overtube assembly onto the distal end of the colonoscope, reinserting the colonoscope with overtube assembly, and relocating the diverticulum is completely gone.

Disclosed herein are tools, devices, assemblies, and methods for inverting and closing diverticula in a body lumen. The tools, devices, and assemblies may be configured for endoscopic delivery, e.g., through a working channel of a colonoscope.

A negative pressure may be applied through a diverticulum inverting device within the body lumen directly to an opening to a diverticulum, thereby causing the diverticulum to invert into the diverticulum inverting device within the body lumen. The negative pressure may alternatively be applied non-specifically within the body lumen itself, thereby causing any or at least some diverticula to invert into the body lumen. Either with or instead of a negative pressure, a positive pressure may be applied from outside the body lumen. For example, a positive pressure may be applied to the body cavity within which the body lumen resides (e.g., to the peritoneal cavity, thereby causing any or some diverticula to invert into the colon). Alternatively, a positive pressure may be applied via a laparoscopic tube directly to the diverticulum, causing it to invert into the colon.

A diverticulum can invert into a body lumen and/or into a device including a containment device and a tube or bushing. The device can deploy the bushing around the inverted diverticulum, the bushing being closable to thereby hold the diverticulum in a radially compressed inverted state. Deploying the bushing includes causing heat-shrink material of the bushing to radially inwardly compress by any of a variety of heating methods. Multiple bushings may be loaded in a single device for serial deployment over multiple diverticula.

A laparoscopic device may be used to apply a positive pressure directly to a diverticulum from outside of the body lumen to which the diverticulum is attached. The laparoscopic device may contact the base of a diverticulum. The laparoscopic device can surround the diverticulum within a working channel of the device. A negative pressure line can apply a negative pressure within a portion of the laparoscopic device to holes in contact with tissue surrounding the diverticulum, creating a substantially airtight fit, and a positive pressure can be applied to the working channel, at least partially inverting the diverticulum into the body lumen.

FIG. 1 is a cross-sectional view of a diverticulum 2 of a sigmoid colon. The walls of the colon generally include an outer layer of serosa 4, an inner layer of mucosa 8, and a muscular layer 6, or muscularis, between the mucosa 8 and serosa 4. In the region of a typical diverticulum 2, a hole may exist in the muscular layer 6, in which case the walls of the diverticulum 2 may have only the outer layer of serosa 4 and the inner layer of mucosa 8. A submucosal region 7 also exists between the mucosa 8 and serosa 4 layers. A diverticulum 2 typically bulges one to two centimeters through the colon wall.

Figure 2:
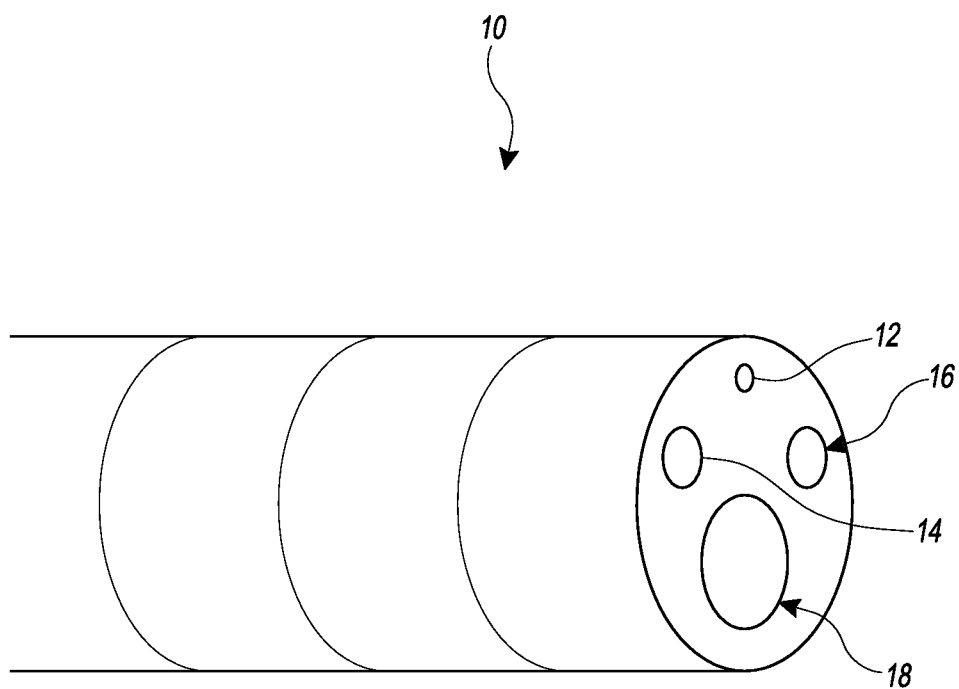
FIG. 2 is a side perspective view of the working end of a colonoscope.
Figure 3:
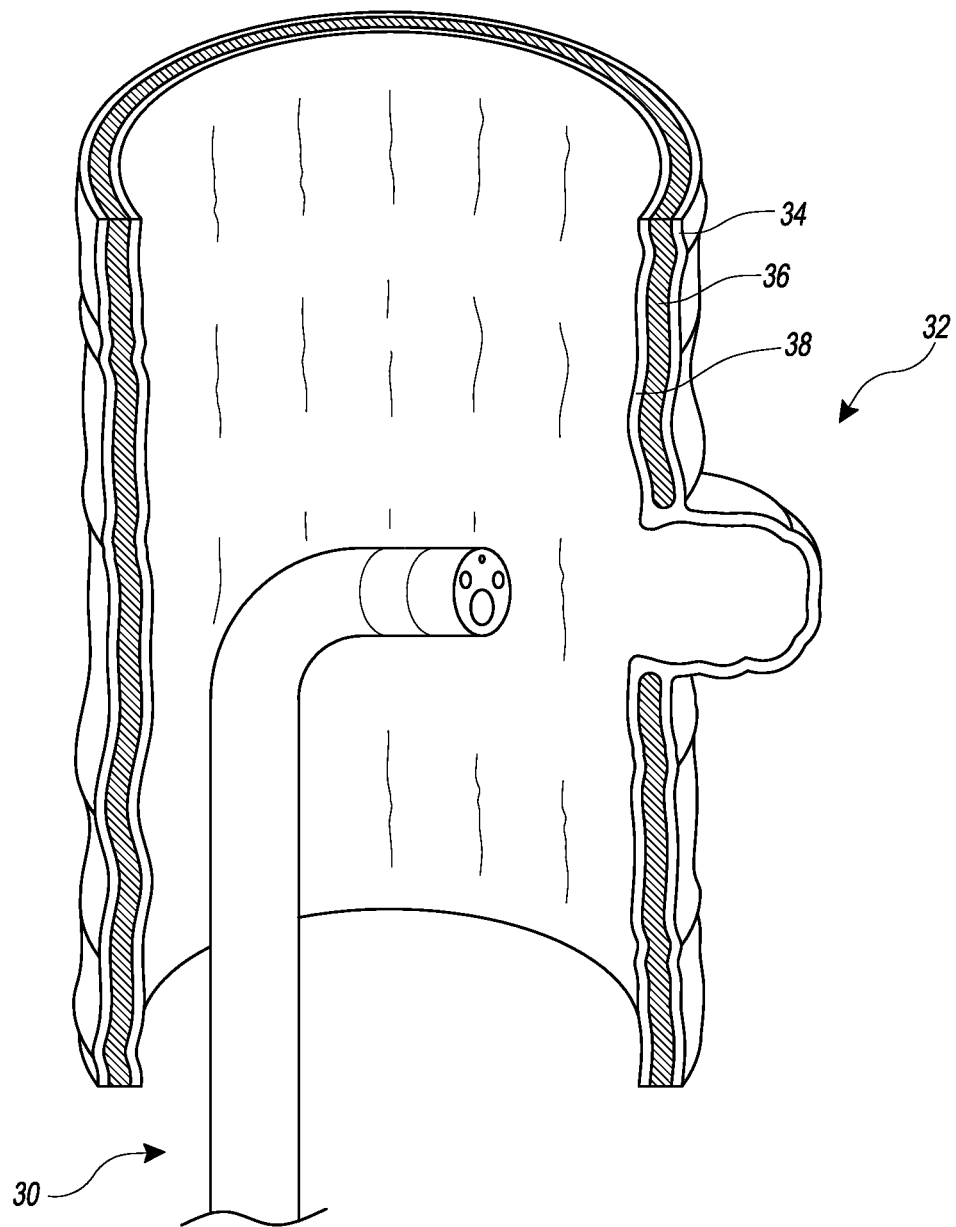
FIG. 3 is a perspective view of a colonoscope bent to view a diverticulum, which is shown in cross-section.

FIG. 2 is a side perspective view of the working end of a colonoscope 10. The colonoscope 10 generally includes one or more of a light source 12 useful to illuminate the area of viewing; a viewing lens 14; a lumen 16, which can include a source of liquid such as water or saline, a source of air, and/or a source of negative pressure; and a working channel 18 through which tools such as biopsy forceps, graspers, or manipulators are typically passed. Colonoscopes 10 are flexible and can be manipulated to bend and articulate along segments up to 180°. For example, as illustrated in FIG. 3, a colonoscope 30 can bend 90° to view a diverticulum 32 (otherwise referred to herein as a "tick"). Once the operator of the colonoscope 30 sees the diverticulum 32, they can position the colonoscope 30 proximate to the diverticulum 32 and prepare to deliver a device through the working channel to reach a diverticulum 32.

Although described in more detail below, the device most basically includes a containment device and a bushing. Referring again to FIG. 2, the containment device can be delivered through the working channel 18 of a colonoscope 10, or can be or integrated with the working channel 18 of the colonoscope 10. The bushing can be provided in a first tubular shape, and can assume or transform toward a second shape or any intermediate shape between the first and second shape upon application of heat. For ease of description, the first shape may be referred to herein as an expanded or delivery configuration and the second shape may be referred to herein as a collapsed configuration.

At least a portion of the inverted diverticulum 2 can be positioned into a first open end of the bushing. Heat can be applied in any one of a variety of manners to heat-shrink material of the bushing so that the bushing transforms from the first tubular state toward a second shape. The bushing can maintain the diverticulum 2 in radially compressed inverted or secured state, allowing the diverticulum 2 to heal on the serosa 8 side and necrose on the mucosa 4 side due, for example due to restricted blood flow, eventually being absorbed or falling off. The secured diverticulum 2 may be cauterized by applying heat. This is a simple process that can be repeated for each diverticulum 2, and may save the patient the significant risk of colon removal surgery.

Figure 4A:
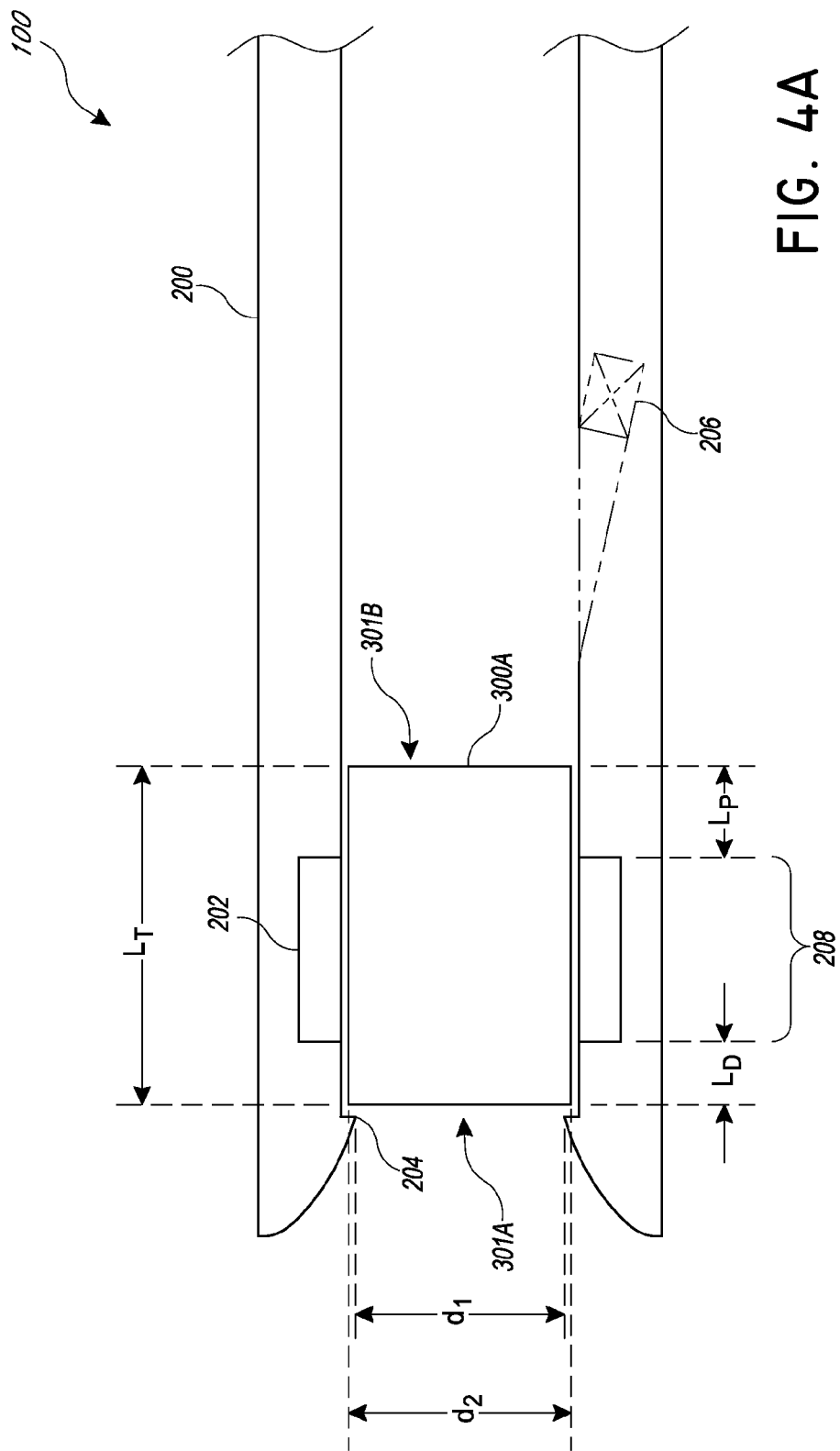
FIGS. 4A and 4B are partial cross-sectional side views of an example embodiment of a device including a containment device and a bushing.
Figure 4B:
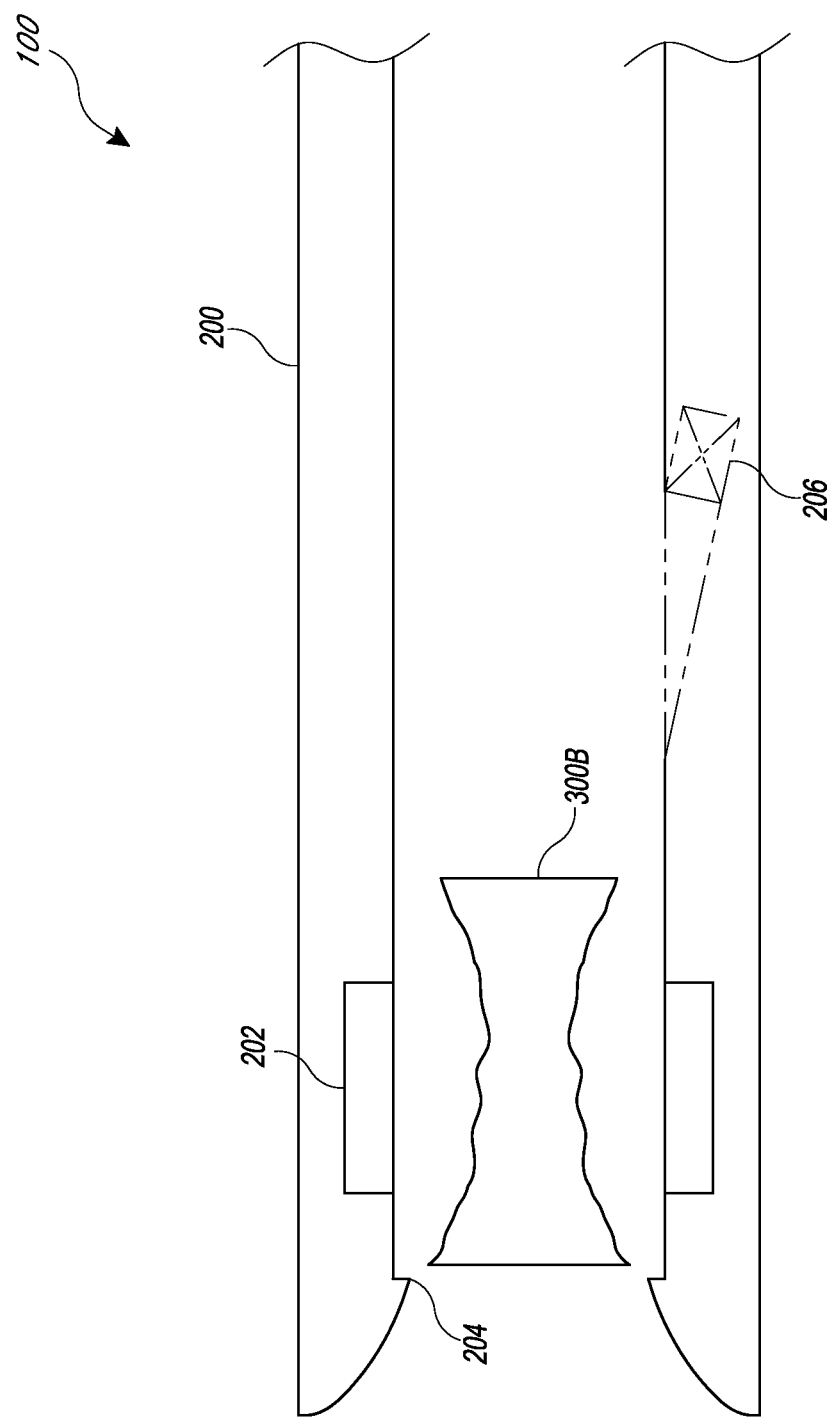

FIGS. 4A and 4B are partial cross-sectional side views of an example embodiment of a device 100 including a containment device 200 and a bushing 300A, 300B. The device 100 can be sized to fit within the working channel of the colonoscope, or can be or integrated with the working channel of the colonoscope. A working channel of a colonoscope typically has a diameter between two and three millimeters, although the containment device 200 and/or the working channel can be larger or smaller.

The containment device 200 includes a conduit or lumen. The bushing 300A is in the conduit of the containment device 200. The bushing 300A includes a first open end or distal end 301A and a second open end or proximal end 301B. Negative pressure can be applied to the conduit while the containment device 200 is in a body lumen to a diverticulum (e.g., through the bushing 300A), thereby causing the diverticulum to invert into the body lumen or at least partially into the conduit of the containment device 200 within the body lumen (e.g., and at least partially into the first open end 301A of the bushing 300A). The negative pressure may alternatively be applied non-specifically within the body lumen itself, thereby causing any or at least some diverticula to invert into the body lumen. Either with or instead of application of negative pressure to the conduit of the containment device 200, positive pressure may be applied from outside the body lumen. For example, positive pressure may be applied to the body cavity within which the body lumen resides (e.g., to the peritoneal cavity, thereby causing any or some diverticula to invert into the colon).

The bushing 300A includes a heat-shrink material. Heat-shrink tubing is generally extracted at a first diameter and then mechanically expanded to a second diameter larger than the first diameter. Upon heating, the heat-shrink tubing reverts towards the first or extrusion diameter. The entire bushing 300A may include heat-shrink material (e.g., is heat-shrink tubing), or a portion of the bushing 300A may include heat-shrink material. As illustrated in FIG. 4A, the bushing 300A is in a first tubular state or an expanded configuration. As illustrated in FIG. 4B, the bushing 300B is in a second state or a collapsed or compressed configuration. The bushing 300A is configured to transform from the first tubular shape toward a second shape upon heating the heat-shrink material. The second shape is radially inward of the first tubular shape.

The heat-shrink material may include, for example, nylon, thermoplastic such as polyolefin, fluoropolymer (e.g., fluorinated ethylene propylene (FEP), polytetrafluoroethylene (PTFE), polyvinylidene fluoride (PVDF)), polyvinyl chloride (PVC), polycholorprene, silicone elastomer, combinations thereof, and the like. A heat-shrink material that is not biocompatible can be coated with a biocompatible polymer. The heat-shrink material may be cross-linked by exposure to radiation (e.g., electron beam, gamma radiation, UV light), oxidizing agents (e.g., peroxide, ethylene oxide), aldehyde, combinations thereof, and the like, which can help maintain shape of the bushing 300 before and/or after heating of the heat-shrink material. Certain such cross-linking processes may also be useful for sterilization of the bushing 300A.

In the example embodiment of the device 100 illustrated in FIG. 4A, the containment device 200 includes a heating element 202 configured to provide heat to the heat-shrink material of the bushing 300A. The heating element 202 may include, for example, a resistive heating element (e.g., including a tungsten wire, a ceramic block, and the like). The heating element 202 may include a unitary heating element or a plurality of heating elements. Application of a voltage or electrical current to the heating element 202 increases the temperature of the heating element 202, and the heat is transferred to the bushing 300A. Upon application of the heat, the heat-shrink material of the bushing 300A causes the bushing 300A to transform from the first tubular state toward a second shape (e.g., depending on counteracting forces such as a diverticulum within the bushing 300A), as illustrated by the bushing 300B in FIG. 4B.

A section of the containment device 200 proximate to the heating element 202 may be thermally insulated to promote heat transfer to the bushing 300A (e.g., primarily to the bushing 300A) and/or to inhibit or prevent heat transfer out of the containment device 200 (e.g., to the body lumen and/or to a colonoscope). For example, the section of the containment device 200 radially outward of the heating element 202 may include a high temperature plastic and/or spun silicon dioxide ($SiO_2$). Other sections of the containment device 200 such as distal to the heating element 202 and proximal to the heating element 202 (e.g., until about the second open end 301B of a bushing 300A) may also be thermally insulating.

The heating element 202 has a longitudinal length 208, which may be less than a longitudinal length $L_T$ of the bushing 300A. Heat transfer may be radially inward from the heating element 202 to the bushing 300, and then disperse longitudinally in the bushing 300A such that the entire bushing 300A does not need to be heated. In the embodiment illustrated in FIG. 4A, the heating element 202 is spaced from the first open end 301A of the bushing 300A by a length $L_D$ and is spaced from the second open end 301B of the bushing 300A by a length L. A longer $L_D$ can reduce heat transfer distal to the bushing 300A (e.g., to the walls of the body lumen). In some embodiments, the length $L_D$ is at least about 20% of the length $L_T$. A longer $L_p$ can reduce heat transfer proximal to the bushing 300A (e.g., to a proximate or adjacent second bushing proximal to the busing 300A in the conduit of the containment device 200). In some embodiments, the length $L_p$ is at least about 20% of the length $L_T$. Longer overlap between the heating element 202 and the bushing 300A can cause more of the bushing 300A to be affected by heat from the heating element 202, which can reduce transformation duration, increase transformation uniformity, and/or the like.

The containment device 200 includes a radially inward protrusion 204 distal to the bushing 300A. The radially inward protrusion 204 has an inner diameter $d_1$. The bushing 300A in the first tubular state has an outer diameter $d_2$. The inner diameter $d_1$ of the radially inward protrusion 204 is less than the outer diameter $d_2$ of the bushing 300A such that the radially inward protrusion 204 inhibits or prevents the bushing 300A from exiting the containment device 200 in the first tubular shape. The radially inward protrusion 204 may be fully annular, partially annular (e.g., a plurality of protrusions), or a single protrusion (e.g., a tooth). Referring again to FIG. 4B, when the bushing 300B is in a second state or a collapsed or compressed configuration, the inner diameter $d_1$ of the radially inward protrusion is not less than the outer diameter of the bushing 300B such that the bushing 300B may exit the containment device 200.

FIG. 4C is a partial cross-sectional side view of another example embodiment of a device 102 including a containment device 201 and a bushing 300C. In contrast to the containment device 200 illustrated in FIGS. 4A and 4B, the containment device 201 does not include the radially inward protrusion 204. The containment device 201 includes an inner surface 203 configured to frictionally inhibit or prevent the bushing 300C from exiting the containment device 201 in the first tubular shape. For example, the inner surface 203 of a distal section of the containment device 201 may be roughened or textured (e.g., by chemical etching, plasma etching, mechanical grinding, and/or lack of polishing, the latter possibly reducing manufacturing costs). The containment devices described herein may include both a radially inward protrusion 204 and an inner surface 203, and/or other means for inhibiting or preventing the bushing from exiting the containment device in the first tubular shape (e.g., magnetic means, adhesive means, etc.).

In the example embodiment of the device 102 illustrated in FIG. 4C, the containment device 201 includes a heating element 232 configured to provide heat to the heat-shrink material of the bushing 300C. The heating element 232 may include, for example, a resistive heating element (e.g., including a tungsten wire, a ceramic block, and the like). The heating element 232 may include a unitary heating element or a plurality of heating elements. Application of a voltage or electrical current to the heating element 232 increases the temperature of the heating element 232, and the heat is transferred to the bushing 300C. Upon application of the heat, the heat-shrink material of the bushing 300C causes the bushing 300C to transform from the first tubular state toward a second shape (e.g., depending on counteracting forces such as a diverticulum within the bushing 300C), as illustrated by the bushing 300B in FIG. 4B.

In some embodiments, a ratio of the transverse diameter $d_2$ of the bushing (e.g., the bushing 300A, the bushing 300B) to the length $L_T$ of the bushing is between about 0.5:1 and about 2:1 (e.g., about 1:1). Smaller ratios can improve navigability (e.g., ease of bending) of the device 100, reduce material costs, and/or reduce heating area. Larger ratios can reduce the propensity of the bushing to non-circumferential rotation (e.g., end-to-end rotation) and/or reduce the risk of heating a proximal bushing in the conduit of the containment device.

Referring again to FIGS. 4A and 4B, the containment device 200 includes an optional imaging system 206. Although not illustrated, other containment devices described herein (e.g., the containment device 201, the containment device 210, the containment device 220, the containment device 250) can include an optional imaging system. The imaging system 206 may include a camera configured to monitor transformation of the bushing, positioning of a diverticulum at least partially into the first open end of the bushing, longitudinal advancement of the bushing, etc. The imaging system 206 may include an optical and/or infrared camera, for example embedded in a wall of the containment device 200 and configured to detect images through a slot proximal to the bushing (e.g., between bushings of a plurality of bushings). The camera may include an x-ray or other type of radiation-emitting camera and the bushing includes radiopaque material viewable under fluoroscopy. In embodiments in which the imaging system 206 is directed between gaps between bushings, a flap or other mechanism may provide a gap between the distal-most bushing and the next distal-most bushing.

Figure 5A:
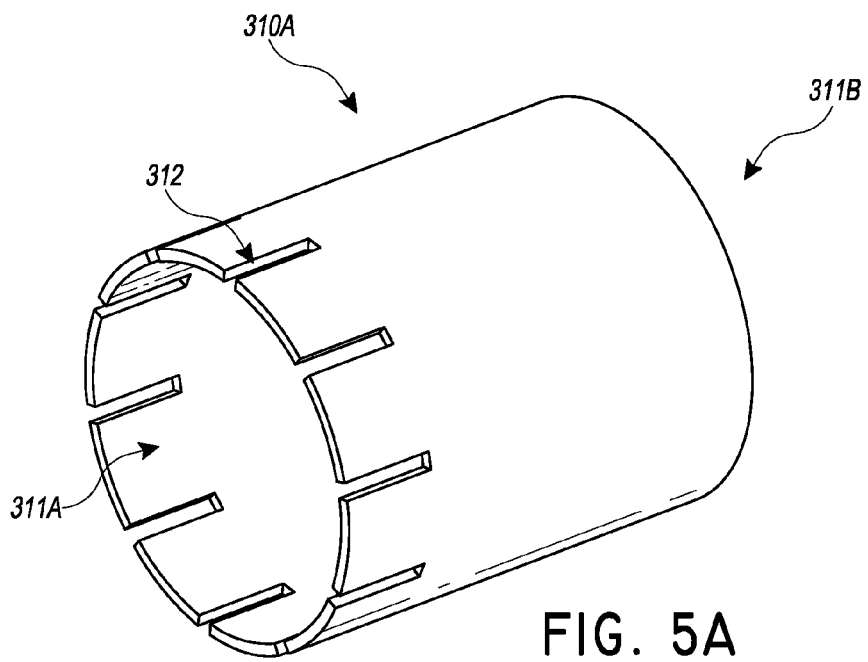
FIGS. 5A and 5B are perspective views of an example embodiment of a bushing.
Figure 5B:
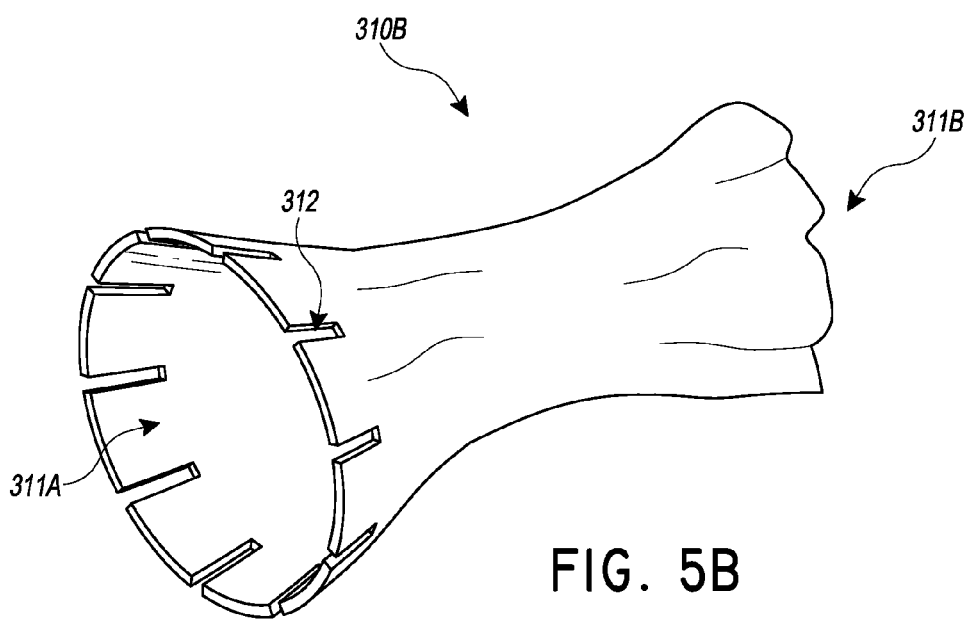

FIGS. 5A and 5B are perspective views of an example embodiment of a bushing 310A, 310B. The bushing 310A includes a first open end or distal end 311A and a second open end or proximal end 311B. As described with respect to the bushings 300A, 300B, the bushing 310A includes a heat-shrink material. As illustrated in FIG. 5A, the bushing 310A is in a first tubular state or an expanded configuration. As illustrated in FIG. 5B, the bushing 310B is in a second state, which may be a collapsed or compressed configuration. The bushing 310A, 310B is configured to transform from the first tubular shape toward a second shape upon heating the heat-shrink material. The second shape is radially inward of the first tubular shape. In some embodiments, the bushings described herein (e.g., the bushing 300A, the bushing 300C, the bushing 310A, etc.) may comprise, instead of or in addition to the heat-shrink material, a shape-memory alloy such as nitinol that is configured to transform from an first or expanded shape (e.g., the tubular shape of the bushings 300A, 300C, 310A) at a first temperature to a second or compressed state (e.g., the shape of the bushings 300B, 310B) at a second temperature.

The first open end 311A includes a plurality of longitudinal slots 312 forming a slotted edge. The slots 312 are configured to face a diverticulum and allow the slotted edge to flare outwards to inhibit or prevent a sharp edge or corner from biting into or cutting the wall of the body lumen (e.g., colon). The slots 312 can soften the edge of the bushing 310A and reduce risk of tearing the diverticulum or wall of the body lumen.

The use and quantity of slots 312 may be influenced, for example, based on the thickness of the bushing 310A. If the thickness is small, the bushing 310A may be more prone to cut into the colon wall because a cylindrical bushing 310A can act as a face mill or hollow mill cutter such that slots 312 that deform before cutting the wall of the body lumen may be desirable. As thickness increases, the edge is more likely to be blunt such that slots 312 that deform may be less desirable.

Biting into or cutting the wall of the body lumen, or proximate to the mouth of a diverticulum, may be desirable, for example to inhibit the diverticulum from sliding out of the bushing 310A. Rather than flaring outwards, the slotted edge can be configured to shrink radially inwardly to effect or enhance biting into or cutting the wall of the body lumen.

Remaining portions of the bushing 310A between the slots 312 sharpened or formed into a point to enhance such biting or cutting.

The bushing 310A, or any of the bushings described herein, may include an inner surface configured to frictionally inhibit or prevent a diverticulum from sliding out of the bushing 310A. For example, the inner surface or a portion of the inner surface of the bushing 310A may be roughened or textured (e.g., by chemical etching, plasma etching, mechanical grinding, an outwardly-textured initial extrusion die, combinations thereof, and the like). A bushing 310A including slots 312 and an inner surface configured to frictionally inhibit or prevent a diverticulum from sliding out of the bushing 310A can include a softened edge to inhibit or prevent a sharp edge or corner from biting into or cutting the wall of the body lumen (e.g., colon), as well as frictionally inhibit or prevent a diverticulum from sliding out of the bushing 310A.

Figure 6A:
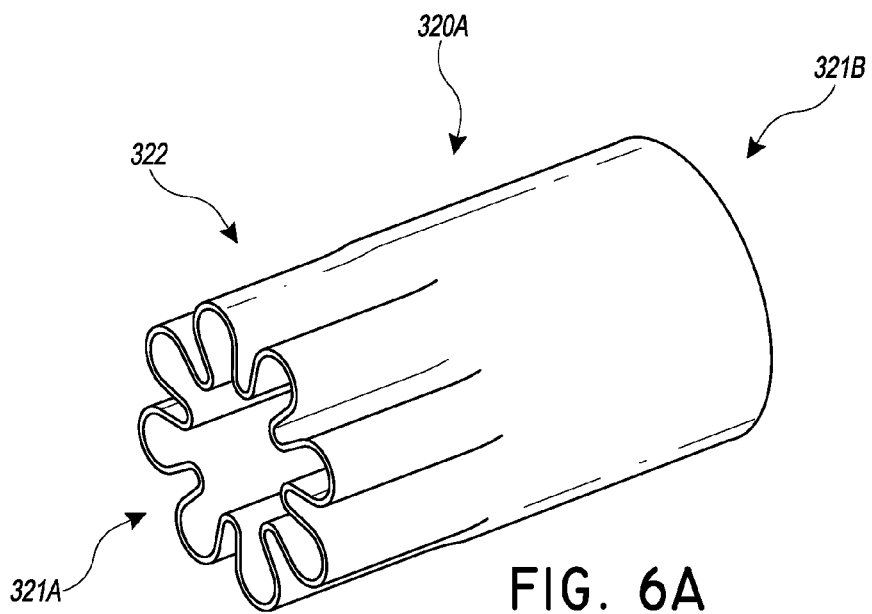
FIGS. 6A-6C are perspective views of another example embodiment of a bushing.
Figure 6B:
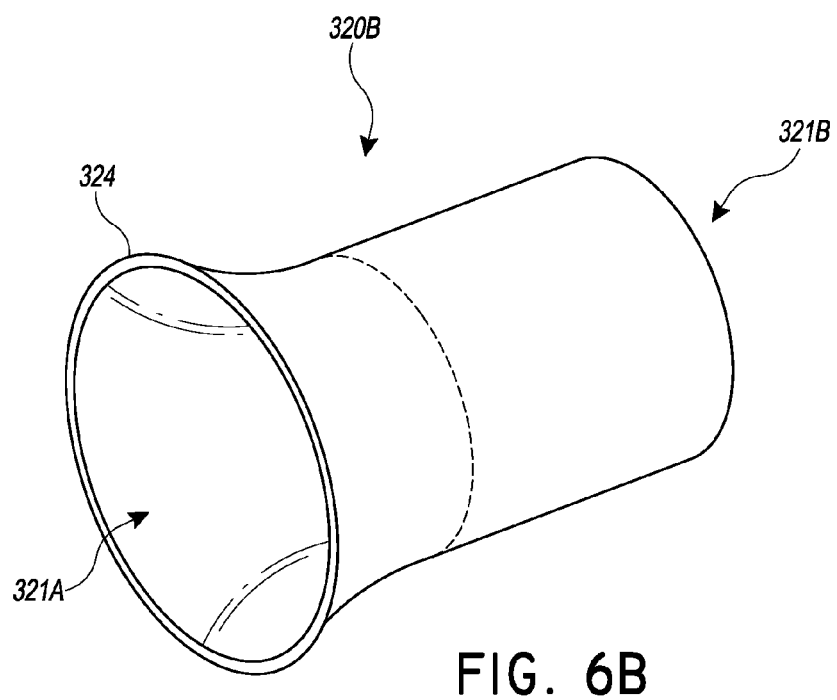
Figure 6C:
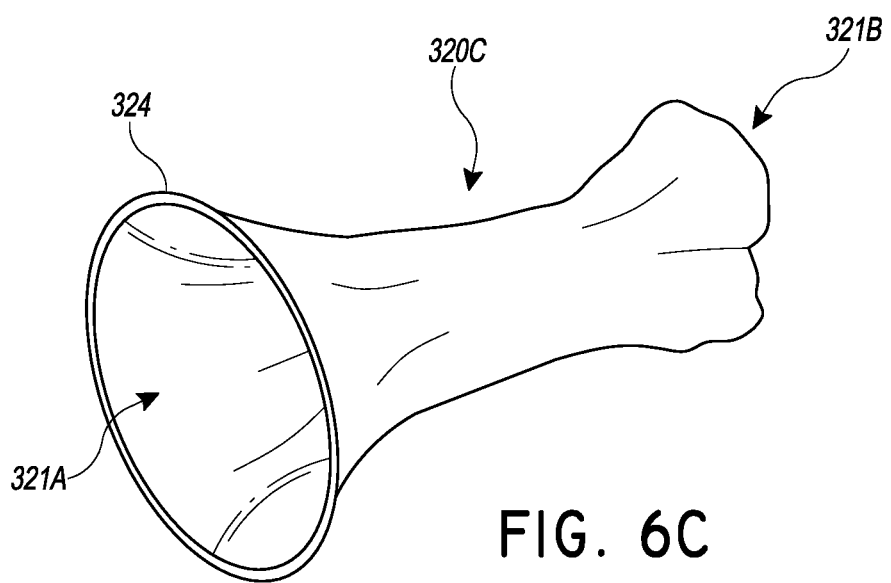

FIGS. 6A-6C are perspective views of another example embodiment of a bushing 320A, 320B, 320C. The bushing 320A, 320B, 320C includes a first open end or distal end 321A and a second open end or proximal end 321B. As described with respect to the bushings above, the bushing 320A includes a heat-shrink material (and/or shape-memory material such as nitinol). As illustrated in FIG. 6A, the bushing 320A is in a first tubular state or an expanded configuration, for example with the first open end 321A being folded to fit within a conduit of a containment device. The bushing 320BA as illustrated in FIG. 6A may be the shape of the bushing 320A when acted upon by inward radial forces (e.g., when the bushing 320A is in a lumen that is smaller than the distal end 321A). As illustrated in FIG. 6B, the bushing 320B is in a third state or a second expanded configuration, for example prior to being in a conduit of a containment device, which includes a trumpeted distal end including a ring 324. The bushing 320B as illustrated in FIG. 6B may be the shape of the bushing 320B when not acted upon by any forces (e.g., sitting on a table). As illustrated in FIG. 6C, the bushing 320C is in a second state or a collapsed or compressed configuration. The bushing 310A is configured to transform from the first tubular shape of FIG. 6A and/or the third tubular shape of FIG. 6B toward a second shape (e.g., as illustrated in FIG. 6C) upon heating the heat-shrink material. The second shape is radially inward of the first tubular shape, even though the ring 324 has the same or substantially the same shape as shown in FIG. 6B. The bushing 320C as illustrated in FIG. 6C may be the shape of the bushing 320C after being heated, either from the first tubular shape illustrated in FIG. 6A or the third tubular shape of FIG. 6B.

The trumpeted distal end and the ring 324 can be shaped to sit more evenly around the base of an inverted diverticulum, act as a nozzle during application of negative pressure to the body lumen, and/or act as a funnel to aid in positioning an inverted diverticulum at least partially into the bushing 320A, 320B. The ring 324 can include a material other than a heat-shrink material to at least partially maintain the trumpeted distal end when the bushing 320B is in the third state (e.g., a polymer ring, a metal ring).

The ring 324 can be radially outwardly biased, which may inhibit or prevent the bushing 320A, 320B from exiting the conduit of a containment device, for example due to frictional engagement with an inner surface (e.g., the inner surface 203 of the containment device 201 described with respect to FIG. 4C). After the ring 324 extends distally past the inner surface, for example when the bushing 320C is ready to be deployed, the ring 324 may expand and the bushing 320B may assume the third state, with sections of the bushing 320B proximal to the trumpeted distal end 321A remaining in the conduit of the containment device for heat application.

The ring 324 can be radially outwardly biased, which may inhibit or prevent the bushing 320A, 320B from exiting the conduit of a containment device, for example due to engagement of a radially inward protrusion (e.g., the radially inward protrusion 204 of the containment device 200 described with respect to FIGS. 4A and 4B) at the distal end of the containment device. After the ring 324 extends distally past a cylindrical portion of the conduit into an outwardly flared portion of the conduit, for example when the bushing 320B is ready to be deployed, the ring 324 may expand and the bushing 320B may assume the third state, with sections of the bushing 320B proximal to the trumpeted distal end 321A remaining in the conduit of the containment device for heat application. The bushing 320C may be released from the conduit of the containment device upon distal advancement of the bushing 320C with force allowing the ring 324 to push past the radially inward protrusion, proximal retraction of the containment device with frictional or other force allowing the bushing 320C to maintain its position such that the ring 324 can push past the radially inward protrusion, combinations thereof, and the like.

FIGS. 7A and 7B are partial cross-sectional side views of an example embodiment of a device 104 including a containment device 210 and a bushing 330A, 330B. The device 104 can be sized to fit within the working channel of a colonoscope, or can be or integrated with the working channel of a colonoscope.

Referring again to FIG. 7A, the containment device 210 includes a conduit or lumen. The bushing 330A is in the conduit of the containment device 210. The bushing 330A includes a first open end or distal end 331A and a second open end or proximal end 331B. Negative pressure can be applied to the conduit while the containment device 210 is in a body lumen to a diverticulum (e.g., through the bushing 330A), thereby causing the diverticulum to invert into the body lumen or at least partially into the conduit of the containment device 210 within the body lumen (e.g., and at least partially into the first open end 331A of the bushing 330A). The negative pressure may alternatively be applied non-specifically within the body lumen itself, thereby causing any or at least some diverticula to invert into the body lumen. Either with or instead of application of negative pressure to the conduit of the containment device 210, positive pressure may be applied from outside the body lumen. For example, positive pressure may be applied to the body cavity within which the body lumen resides (e.g., to the peritoneal cavity, thereby causing any or some diverticula to invert into the colon).

Figure 8:
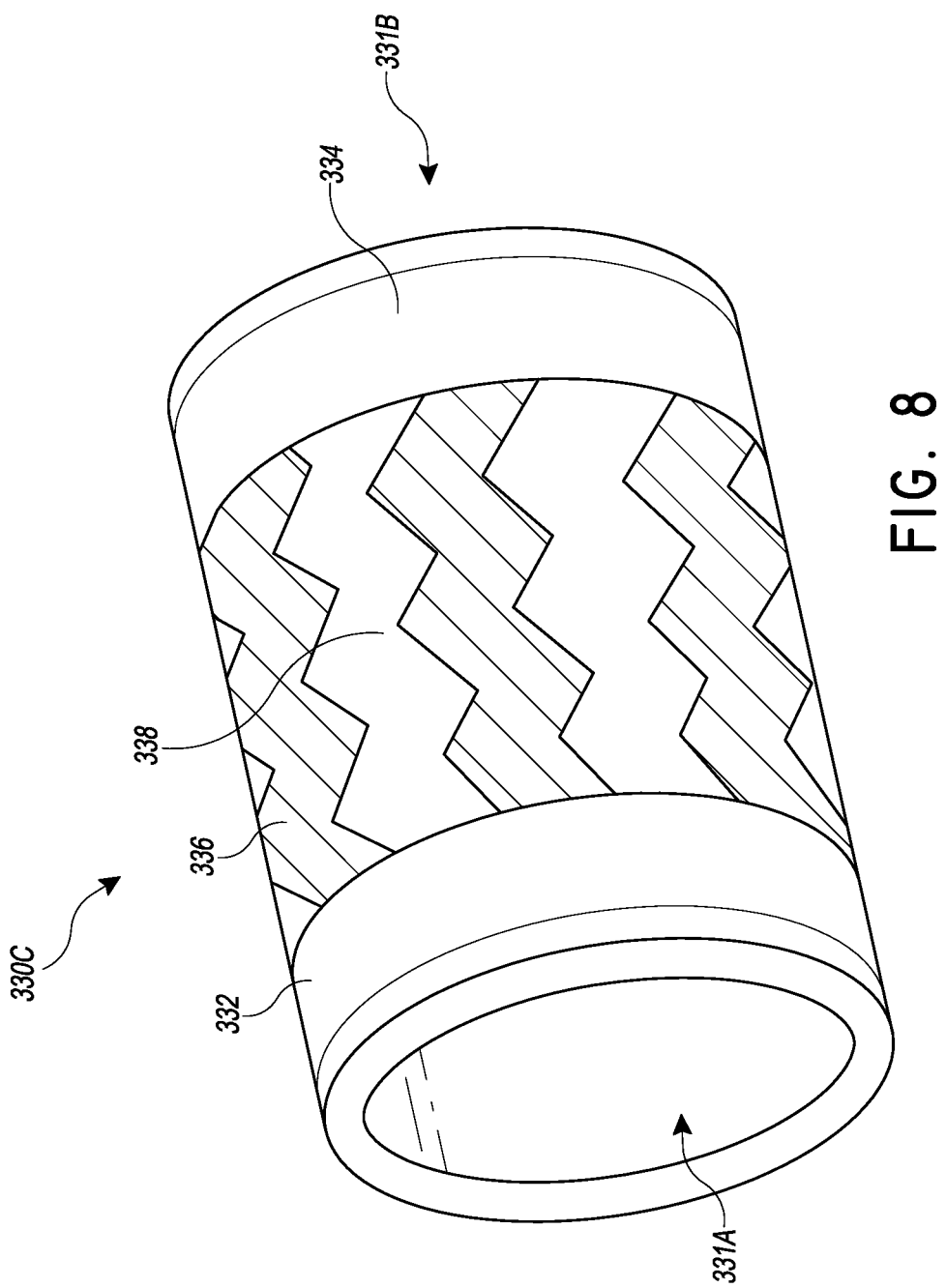
FIG. 8 is a perspective view of an example embodiment of a bushing.

FIG. 8 is a perspective view of an example embodiment of a bushing 330C. The bushing 330C includes a first electrically conductive track 332, a second electrically conductive track 334, and an ohmic resistor between the first electrically conductive track 332 and the second conductive track 334. The bushing 330C includes a heat-shrink material 338. As illustrated in FIGS. 7A and 8, the bushing 330A, 330C is in a first tubular state or an expanded configuration. As illustrated in FIG. 7B, the bushing 330B is in a second state or a collapsed or compressed configuration. The bushing 330A, 330C is configured to transform from the first tubular shape toward a second shape upon heating the heat-shrink material. The second shape is radially inward of the first tubular shape.

In the example embodiment of the device 100 illustrated in FIG. 4A, the containment device 200 includes a heating element 202 configured to provide heat to the heat-shrink material of the bushing 300A by thermal radiation. In the example embodiment of the device 104 illustrated in FIG. 7A, the containment device 210 includes a first contact 212A configured to conduct electrical current to the first electrically conductive track 332 and a second flexible contact 212B configured to conduct electrical current to the second electrically conductive track 334. At least one of the first contact 212A and the second contact 212B may include a spring contact biased radially inwardly (e.g., sprung or woven wire) or other means for maintaining contact between a contact 212A, 212B and an electrically conductive track 332, 334. Application of a voltage or electrical current to the first contact 212A and/or the second contact 212B can increase the temperature of the ohmic resistor 336, and the heat is directly transferred to the heat-shrink material 338 of the bushing 330A. Upon application of the heat, the heat-shrink material of the bushing 330A causes the bushing 330A to transform from the first tubular state toward a second shape (e.g., depending on counteracting forces such as a diverticulum within the bushing 330A), as illustrated by the bushing 330B in FIG. 7B.

Direct heat transfer to the heat-shrink material of the bushing 330A can inhibit or prevent heat transfer out of the containment device 210 (e.g., to the body lumen and/or to a colonoscope), even without a section of the containment device 210 including a high temperature plastic and/or spun $SiO_2$, although such thermal insulation may still be desirable due to heat emitted by the ohmic resistor 336.

The containment device 210 includes a radially inward protrusion 214 distal to the bushing 330A, which can, for example as described above with respect to the containment device 200, inhibit or prevent the bushing 330A from exiting the containment device 210 in the first tubular shape. The containment device 210 may also or alternatively include an inner surface configured to inhibit or prevent the bushing 330A from exiting the containment device 210 in the first tubular shape, for example as described above with respect to the inner surface 203 of the containment device 201. The containment device 210 may also include an imaging system or other features described with respect to other containment devices described herein.

Referring again to FIG. 8, one or both of the electrically conductive tracks 332, 334 may include a conductive biocompatible material such as aluminum or conductive polymer. The electrically conductive tracks 332, 334 may be fully annular or partially annular (e.g., in embodiments in which the bushing 330A is shaped or otherwise configured to maintain a rotational position within the conduit of the containment device 210). The ohmic resistor 336 may include a conductive biocompatible material such as tungsten or conductive polymer. The ohmic resistor 336 may be in the shape of a plurality of zig-zags, straight wires, a coil, a monolithic shell, combinations thereof, and the like. Certain patterns may increase heat transfer to the heat-shrink material 338 of the bushing 330A. The electrically conductive tracks 332, 334 and/or the ohmic resistor 336 may be formed on the heat-shrink material 338, for example by deposition on heat-shrink tubing.

Figure 9:
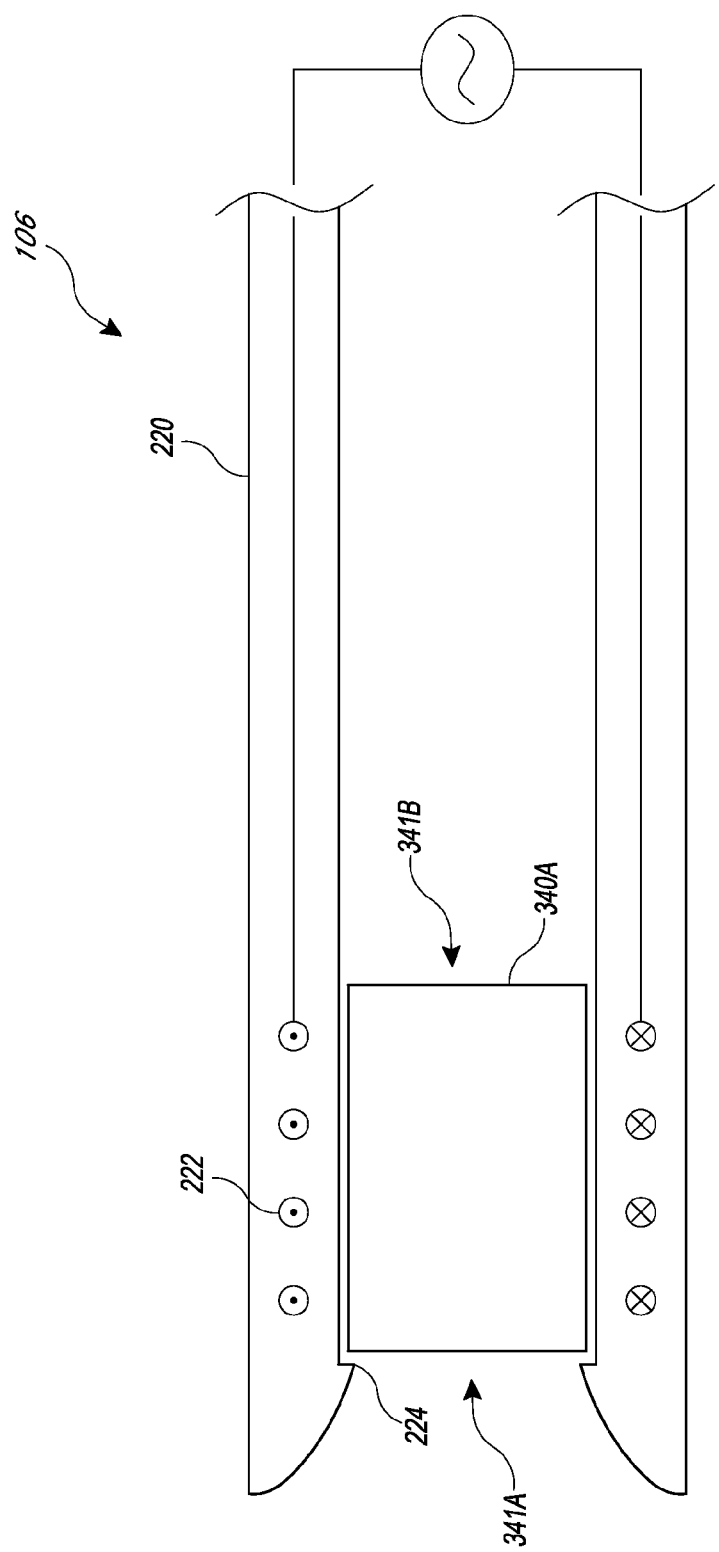
FIG. 9 is a partial cross-sectional side view of an example embodiment of a device including a containment device and a bushing.

FIG. 9 is a partial cross-sectional side view of an example embodiment of a device 106 including a containment device 220 and a bushing 340A. The device 106 can be sized to fit within the working channel of a colonoscope, or can be or integrated with the working channel of a colonoscope.

The containment device 220 includes a conduit or lumen. The bushing 340A is in the conduit of the containment device 220. The bushing 340A includes a first open end or distal end 341A and a second open end or proximal end 341B. Negative pressure can be applied to the conduit while the containment device 220 is in a body lumen to a diverticulum (e.g., through the bushing 340A), thereby causing the diverticulum to invert into the body lumen or at least partially into the conduit of the containment device 220 within the body lumen (e.g., and at least partially into the first open end 341A of the bushing 340A). The negative pressure may alternatively be applied non-specifically within the body lumen itself, thereby causing any or at least some diverticula to invert into the body lumen. Either with or instead of application of negative pressure to the conduit of the containment device 220, positive pressure may be applied from outside the body lumen. For example, positive pressure may be applied to the body cavity within which the body lumen resides (e.g., to the peritoneal cavity, thereby causing any or some diverticula to invert into the colon).

FIG. 10 is a perspective view of an example embodiment of a bushing 340B. The bushing 340B includes heat-shrink material 342 and a foil layer external 344 to the heat-shrink material 342. As illustrated in FIGS. 9 and 10, the bushing 340A, 340B is in a first tubular state or an expanded configuration. As can be appreciated, for example from FIGS. 4B, 5, 6C, and 7B, the bushing 340A, 340B can also be in a second state or a collapsed or compressed configuration. The bushing 340A, 340B is configured to transform from the first tubular shape toward a second shape upon heating the heat-shrink material. The second shape is radially inward of the first tubular shape.

In the example embodiment of the device 100 illustrated in FIG. 4A, the containment device 200 includes a heating element 202 configured to provide heat to the heat-shrink material of the bushing 300A by thermal radiation. In the example embodiment of the device 106 illustrated in FIG. 9, the containment device 220 includes a solenoid 222 configured to conduct create a magnetic field upon the application of alternative current, which can create electrical eddy currents in the foil of the bushing 340A, which can create ohmic resistance heating that can directly transfer heat to the heat-shrink material of the bushing 340A. Upon application of the heat, the heat-shrink material of the bushing 340A causes the bushing 340A to transform from the first tubular state toward a second shape (e.g., depending on counteracting forces such as a diverticulum within the bushing 340A).

Direct heat transfer to the heat-shrink material of the bushing 340A can inhibit or prevent heat transfer out of the containment device 220 (e.g., to the body lumen and/or to a colonoscope 10), even without a section of the containment device 220 including a high temperature plastic and/or spun $SiO_2$, although such thermal insulation may still be desirable due to heat emitted by the foil. Magnetic shielding may be provided outward of the solenoid 222, for example using a thin steel band.

The containment device 220 includes a radially inward protrusion 224 distal to the bushing 340A, which can, for example as described above with respect to the containment device 200, inhibit or prevent the bushing 340A from exiting the containment device 220 in the first tubular shape. The containment device 220 may also or alternatively include an inner surface configured to inhibit or prevent the bushing 340A from exiting the containment device 220 in the first tubular shape, for example as described above with respect to the inner surface 203 of the containment device 201. The containment device 220 may also include an imaging system or other features described with respect to other containment devices described herein.

A containment device may include at least some of the features from the containment devices 200, 201, 210, 220 described herein. For example, a containment device may include two or more of a heating element, contacts, and a solenoid such that the containment device can appropriately effect transformation of a variety of different types of bushings. For another example, a containment device may include contacts configured to effect transformation of a bushing and a heating element configured to cauterize a diverticulum. A solenoid may be effective to effect transformation of a variety of types of bushing (e.g., a bushing 330A and a bushing 340A), advantageously without maintaining electrical contact, which could reduce complexity and increasing tolerances of one or both of the containment device and the bushing.

Referring again to FIG. 10, the foil 344 may include a conductive biocompatible material with low resistance such as aluminum, iron, conductive polymer, etc. The foil may have a thickness between about 0.05 mm and about 0.1 mm. The foil 334 may be in the shape of a plurality of zig-zags, straight wires, a coil, a monolithic shell, combinations thereof, and the like. Certain patterns may increase heat transfer to the heat-shrink material 342 of the bushing 340B. The foil 344 may be formed on the heat-shrink material 342, for example by deposition on heat-shrink tubing. The bushing 340B may include an optional corrosion barrier 346 (e.g., including polymer) external to the foil layer 344.

FIGS. 11A-11D illustrate an example embodiment of a method of treating a diverticulum 302 using a device 110 including a containment device 250 and a bushing 350A. The device 110 may include any of the devices 100, 102, 104, 106 described herein or other devices (e.g., including various combinations of features of the devices 100, 102, 104, 106). The diverticulum 302 is in a body lumen (e.g., a colon).

The containment device 250 includes a conduit or lumen. A plurality of bushings 350 (e.g., 350A, 350B, etc.) are in the conduit of the containment device 250. Each of the bushings 350 includes a first open end or distal end 351A and a second open end or proximal end 351B. Each of the bushings 350 includes a heat-shrink material. The entire bushing 350 may include heat-shrink material (e.g., is heat-shrink tubing), or a portion of the bushing 350 may include heat-shrink material. The bushings 350 may be the same or substantially the same, or the bushings 350 may be different from each other (e.g., some bushings including electrical tracks, a foil, a trumpeted distal end, etc.).

The first open end 351A and the second open end of the bushings 350 include a flared end. Flared ends may allow the bushings 350 to abut each other with reduced or no jamming. For example as described herein with respect to the trumpeted distal end of the bushing 320, flared ends can inhibit or prevent sharp edges that could lacerate a diverticulum 302. Larger wall thicknesses of the bushings 350 could also reduce jamming and/or inhibit laceration. Flared edges in combination with the smaller intermediate diameter can allow the bushes 350 to clear the conduit of the containment system 110 even when bent. One, both, or neither of the first open end 351A and the second open end of the bushings 350 may include a flared end.

The device 110 is positioned proximate to a diverticulum 302, as shown in FIG. 11A. Negative pressure is applied to the conduit while the containment device 250 is in a body lumen containing the diverticulum 302 (e.g., through the bushings 350), thereby causing the diverticulum 302 to invert into the body lumen or at least partially into the conduit of the containment device 250 within the body lumen (e.g., and at least partially into the first open end 351A of the bushing 350, as shown in FIG. 11B). The negative pressure may alternatively be applied non-specifically within the body lumen itself and/or positive pressure may be applied from outside the body lumen, thereby causing any or at least some diverticula (e.g., the diverticulum 302) to invert into the body lumen (e.g., the diverticulum 302 may be inverted prior to positioning of the device 110).

The bushing 350A is transformed from the first tubular shape toward a second shape by heating the heat-shrink material of the bushing 350A in FIG. 11C. The second shape includes at least a portion of the bushing 350A radially inward relative to the first tubular shape. The compressive force of the bushing 350A on the inverted diverticulum 302 may at least partially depend on the composition of the heat-shrink material and/or the thickness of the bushing 350A. Although illustrated as a heating element 252 applying radiation heating, any of the mechanisms described herein (e.g., direct heating via contact and/or induction) are also possible. After transforming the bushing 350A, the bushing 350A in the second state holds the diverticulum in a radially compressed inverted state, as shown in FIGS. 11C and 11D. After transforming the bushing 350A, at least part of the inverted diverticulum extends out of the second open end of the bushing 350A, as shown in FIGS. 11C and 11D, although this may not always occur depending on the length of the bushing 350A and the size of the diverticulum 302.

Heat-shrink material is generally used for electronics, such as coupling soldered wires. Heating the heat-shrink material is generally performed in an open environment, which enables the use of hair dryers or heat guns, open flames, and the like. By contrast, the devices and methods disclosed herein appreciate limitations that may be imposed by heating heat-shrink material within a body lumen and/or by proximate or adjacent bushings that are not yet to be exposed to such heat.

In embodiments in which the containment device includes a heating element, the heating element may be used to at least partially cauterize the secured diverticulum. Other heating elements may also be used, and other treatments of the secured diverticulum are also possible (e.g., ablation, drug application, etc.).

After transforming the bushing 350A, the device 110 is retracted, as shown in FIG. 11D, thereby deploying the bushing out of the conduit of the containment device 250. Although illustrated as being deployed out of a longitudinal end of the containment device 250, the bushing 350A may be deployed out of a side of the containment device 250.

Holding the inverted diverticulum allows the serosa to grow together across the base of the diverticulum 302. Additionally, by joining the serosa, the opening in the muscular layer of the colon wall through which a diverticulum 302 is formed will be reduced, which can preclude circulation of blood into the tissue of the diverticulum 302 and cause necrosis of the diverticulum 302. It may be desirable to deflate the colon slightly in order to create contact between the serosa. The necrotized diverticulum may slough off while the serosa at the base of diverticulum will begin to adhere to itself and heal. The treated diverticulum can be removed with a RF snare, cautery wire, blade, or other removal implement, either using the device 110 or a different device.

Without withdrawing the containment device 252 from the body lumen, the bushing 350B may be distally advanced in the conduit of the containment device 252, ready for treatment of a second diverticulum. Treatment of a second diverticulum may proceed according to the method described with respect to FIGS. 11A-11D, or a modification thereof (e.g., if the bushing 350A is different than the bushing 350B, a different transformation method may be used). A plurality of any of the bushings described herein may be longitudinally loaded into the conduit of the containment device 252.

A plurality or train of bushings 350 in a single containment device 250 can enable treatment of a plurality of diverticula within a body lumen by serial deployment without withdrawing the containment device 250. This can advantageously reduce duration in an operating theater, which can reduce medical care costs, reduce risk of infection, allow more procedures to be performed, etc.

During the process illustrated in FIGS. 11A-11D or a portion thereof, an imaging device of the containment device 250 may be used. For example, the imaging device may monitor inversion of the diverticulum 302, positioning of the inverted diverticulum 302, transformation of the bushing 350A, advancement of the bushing 350B, etc. The bushings 350 may be advanced using an advancement member (e.g., including a spring or other device to automatically push the bushings 350 forward upon deployment of the bushing 350A, a coil or push tube to manually push the bushings 350 forward at the discretion of the user, etc.). The advancement member may include markings (e.g., indicative of the number of bushings 350 remaining, indicative of how far to advance to fully advance the bushings 350, etc.). The actuation member may be hollow to allow for flow of material (e.g., saline or drugs into the conduit, or fecal matter or ablated diverticula out of the conduit) and/or application of pressure in or out of the conduit. The actuation member may be actuatable using a trigger (e.g., as in a ratchet or a musket loader). The device 150 may include a first trigger for effecting transformation of the bushings 350 and a second trigger for effecting advancement of the bushings 350.

Figure 12A:
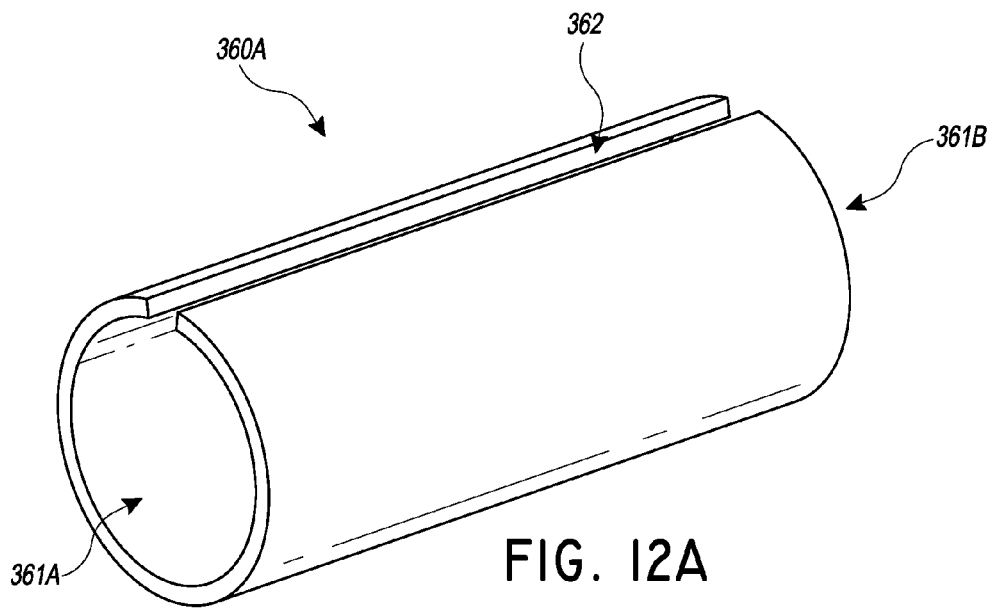
FIGS. 12A and 12B are perspective views of yet another example embodiment of a bushing.
Figure 12B:
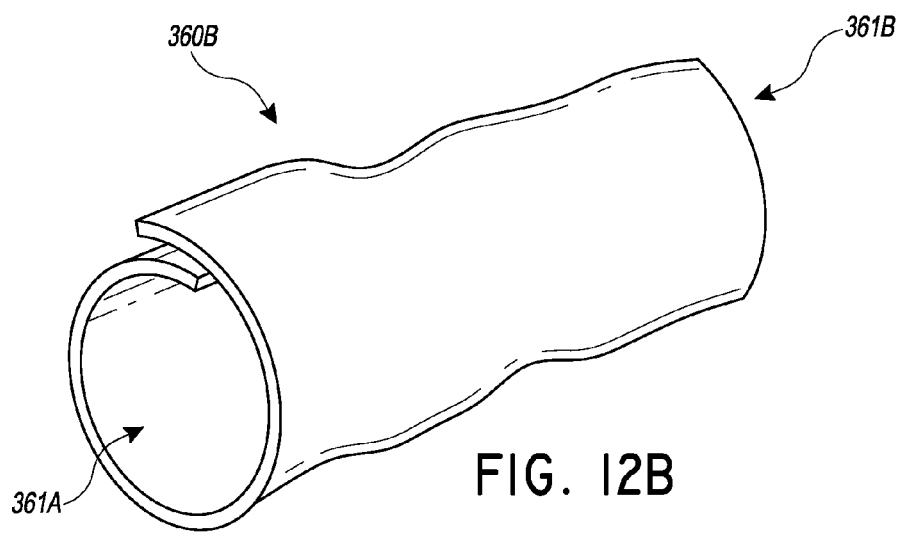

FIGS. 12A and 12B are perspective views of yet another example embodiment of a bushing 360A, 360B. The bushing 360A includes a first open end 361A, a second open end 361B, and a longitudinal slot 362 between the first open end 361A and the second open end 361B. The bushing 360A includes heat-shrink material. As illustrated in FIG. 12A, the bushing 360A is in a first tubular state or an expanded configuration. As illustrated in FIG. 12B, the bushing 360B can also be in a second state or a collapsed or compressed configuration. The bushing 360A is configured to transform from the first tubular shape toward a second shape upon heating the heat-shrink material. The second shape is radially inward of the first tubular shape. The longitudinal slot 362 allows the bushing 360A to fold in upon itself during contraction, as shown by the overlap in the bushing 360B in FIG. 12B, which can increase contraction of a diverticulum.

Figure 13A:
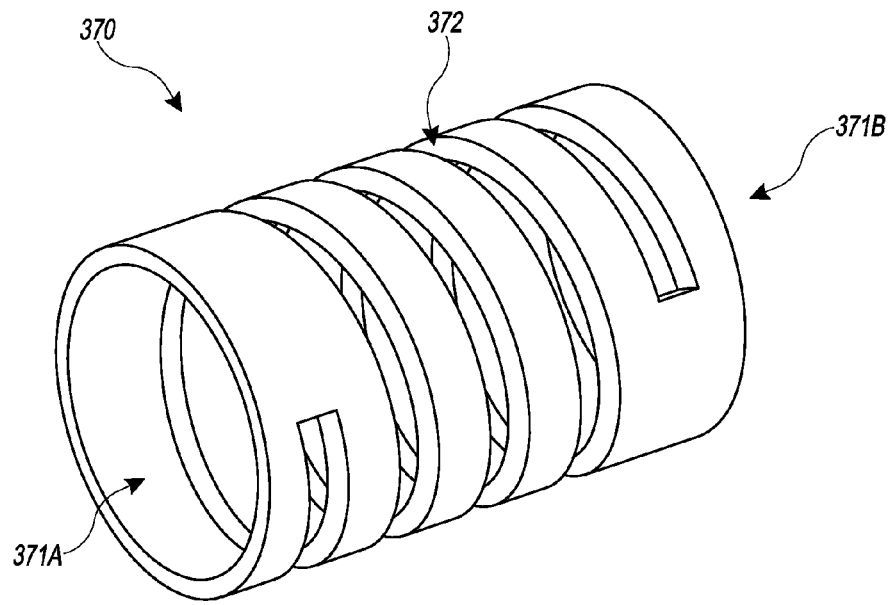
FIG. 13A is a perspective view of still another example embodiment of a bushing.

FIG. 13A is a perspective view of still another example embodiment of a bushing 370. The bushing 370 includes a first open end 371A, a second open end 371B, and a spiral cut 372 between the first open end 371A and the second open end 371B. The bushing 370 includes heat-shrink material. As illustrated in FIG. 13A, the bushing 370 is in a first tubular state or an expanded configuration. As can be appreciated, for example from FIGS. 4B, 5, 6C, and 7B, the bushing 370 can also be in a second state or a collapsed or compressed configuration. The bushing 370 is configured to transform from the first tubular shape toward a second shape upon heating the heat-shrink material. The second shape is radially inward of the first tubular shape. The spiral cut 372 increases longitudinal flexibility of the bushing 380, which can enhance navigability of a containment device containing the bushing 380. The spiral cut 372 may increase interaction between the bushing 380 and an inverted diverticulum, for example increasing frictional engagement due to edges of the spiral cut 372.

Figure 13B:
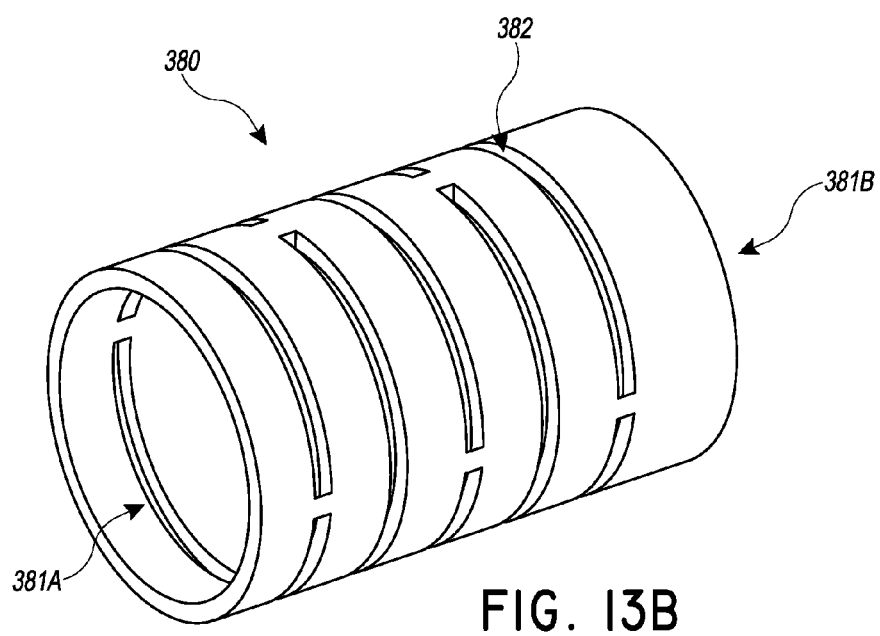
FIG. 13B is a perspective view of still yet another example embodiment of a bushing.

FIG. 13B is a perspective view of still yet another example embodiment of a bushing 380. The bushing 380 includes a first open end 381A, a second open end 381B, and a plurality of transverse slots 382 between the first open end 381A and the second open end 381B. The bushing 380 includes heat-shrink material. As illustrated in FIG. 13B, the bushing 380 is in a first tubular state or an expanded configuration. As can be appreciated, for example from FIGS. 4B, 5, 6C, and 7B, the bushing 380 can also be in a second state or a collapsed or compressed configuration. The bushing 380 is configured to transform from the first tubular shape toward a second shape upon heating the heat-shrink material. The second shape is radially inward of the first tubular shape. The plurality of transverse slots 382 increase longitudinal flexibility of the bushing 380, which can enhance navigability of a containment device containing the bushing 380. Although illustrated as including alternating partially annular transverse slots 382, a wide variety of slot cut patterns are possible. The plurality of transverse slots 382 may increase interaction between the bushing 380 and an inverted diverticulum, for example increasing frictional engagement due to edges of the plurality of transverse slots 382.

Combinations of all of some or all of the features of the bushings 300A, 300B, 300C, 310A, 310B, 320A, 320B, 320C, 330A, 330B, 330C, 340A, 340B, 350, 360, 370, 380 described herein are possible. For example, any of the bushings 300A, 300B, 300C, 310A, 310B, 320A, 320B, 320C, 330A, 330B, 330C, 340A, 340B, 350 may include a longitudinal slot 362, a spiral cut 372, and/or a plurality of transverse slots 382. For another example, any of the bushings 300A, 300B, 300C, 320A, 320B, 320C, 330A, 330B, 330C, 340A, 340B, 350 may include a slotted edge. For yet another example, any of the bushings 300A, 300B, 300C, 310A, 310B, 330A, 330B, 330C, 340A, 340B, 350 may include a trumpeted distal end. For still another example, any of the bushings 300A, 300B, 300C, 310A, 310B, 320A, 320B, 320C, 330A, 330B, 330C, 340A, 340B may include flared ends. For yet still another example, any of the bushings 300A, 300B, 300C, 310A, 310B, 320A, 320B, 320C, 330A, 330B, 330C, 340A, 340B, 350, 360, 370, 380 may include shape-memory material such as nitinol instead of or in addition to heat-shrink material. Other combinations and permutations are also possible.

The devices 100, 102, 104, 106, 110 described herein, and modifications thereof, may be reusable (e.g., sterilizable) or disposable. The number of bushings may be between about 5 and about 25. Lower numbers of bushings may be used to reduce waste upon disposal. Higher numbers of bushings may be useful to ensure that most or all diverticula in a body lumen can be treated without withdrawing the device from the body lumen.

In comparison to certain other diverticulum closing devices (e.g., including shape-memory alloys such as nitinol, complicated snare systems, etc.), the bushings described herein that include heat-shrink material are likely to be relatively inexpensive. Although some of the complexity is transferred to the containment device, the containment device may also be relatively inexpensive compared to other diverticulum closing devices (e.g., restraining shape-memory alloys, complicated snare systems, etc.). The elegance of the bushings described herein that include heat-shrink material provide a platform that allows as much or as little complexity as desired.

While the description generally refers to colonoscopes and treatments within a colon, the devices and methods described herein are not limited to applications within a colon. They can be used to invert and/or treat outpocketings (e.g., diverticula, aneurisms, etc.) in any body lumen. Any reference to a colonoscope should be understood to be applicable to endoscopes generally, and similarly, any reference to a colon should be understood to be applicable to any body lumen.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "between," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration, and are not intended to be limiting, with the true scope and spirit being indicated by the following claims.

EXAMPLE EMBODIMENTS

1. A method of treating a diverticulum of a body lumen, the method comprising:
   positioning the diverticulum in an inverted state at least partially into a first open end of a bushing in an elongate conduit of a containment device, the bushing including a heat-shrink material; and
   transforming the bushing from a first tubular shape including the first open end and a second open end toward a second shape, wherein transforming the bushing includes heating the heat-shrink material, the second shape including at least a portion of the bushing radially inward relative to the first tubular shape, wherein, after transforming the bushing, the bushing in the second shape holds the diverticulum in a radially compressed inverted state.

2. The method of Embodiment 1, wherein the containment device includes a distal end comprising a resistive heating element and wherein heating the heat-shrink material comprises applying current to the resistive heating element.

3. The method of Embodiment 1, wherein the containment device includes a distal end comprising flexible electrical contacts and wherein heating the heat-shrink material comprises applying current to the flexible electrical contacts.

4. The method of Embodiment 1, wherein the containment device includes a distal end comprising a solenoid and wherein heating the heat-shrink material comprises applying current to the solenoid.

5. The method of any one of Embodiments 1-4, wherein, after transforming the bushing, at least part of the inverted diverticulum extends out of the second open end of the bushing.

6. The method of any one of Embodiments 1-5, further comprising cauterizing a mouth of the inverted diverticulum.

7. The method of any one of Embodiments 1-6, further comprising applying pressure to the diverticulum sufficient to cause at least a portion of the diverticulum to invert.

8. The method of Embodiment 7, wherein applying the pressure comprises applying negative pressure within the conduit of the containment device.

9. The method of any one of Embodiments 1-8, further comprising imaging the bushing during transforming the bushing.

10. The method of any one of Embodiments 1-9, wherein the body lumen is a colon.

11. The method of Embodiment 10, wherein a colonoscope comprises the containment device and wherein the method further comprises advancing the colonoscope proximate to the diverticulum.

12. The method of any one of Embodiments 1-11, further comprising deploying the bushing out of the conduit of the containment device.

13. The method of Embodiment 12, wherein deploying the bushing out of the conduit of the containment device comprises deploying the bushing out of a longitudinal end of the containment device.

14. The method of Embodiment 12, wherein deploying the bushing out of the conduit of the containment device comprises deploying the bushing out of a side of the containment device.

15. The method of any one of Embodiments 1-14, further comprising, after transforming the bushing and without withdrawing the containment device from the body lumen,
   distally advancing a second bushing in the conduit of the containment device, the second bushing including a heat-shrink material, a first open end, and a second open end;
   positioning a second diverticulum in an inverted state at least partially into the first open end of the second bushing in the elongate conduit of the containment device; and
   transforming the second bushing from a first tubular shape including the first open end and the second open end toward a second shape, wherein transforming the second bushing includes heating the heat-shrink material, the second shape including at least a portion of the second bushing radially inward relative to the first tubular shape, wherein, after transforming the second bushing, the second bushing in the second shape holds the second diverticulum in a radially compressed inverted state.

16. A device for treating a diverticulum, the device comprising:
   a containment device including an elongate conduit;
   a bushing in the conduit of the containment device, the bushing including a heat-shrink material, the bushing having a first tubular shape including a first open end and a second open end, at least a portion of the diverticulum in an inverted state positionable into the first open end, the bushing configured to transform from the first tubular shape toward a second shape upon heating the heat-shrink material, the second shape including at least a portion of the bushing radially inward relative to the first tubular shape, the bushing in the second shape configured to hold the diverticulum in a radially compressed inverted state.

17. The device of Embodiment 16, wherein the heat-shrink material comprises at least one of nylon, thermoplastic such as polyolefin, fluoropolymer, fluorinated ethylene propylene (FEP), polytetrafluoroethylene (PTFE), polyvinylidene fluoride (PVDF), polyvinyl chloride (PVC), polycholorprene, and silicone elastomer.

18. The device of Embodiment 16 or 17, wherein the containment device includes a distal end comprising a heating element.

19. The device of Embodiment 18, wherein the heating element comprises a resistive heating element.

20. The device of Embodiment 19, wherein the resistive heating element comprises a tungsten wire.

21. The device of Embodiment 19 or 20, wherein the resistive heating element comprises a ceramic block.

22. The device of any one of Embodiments 18-21, wherein the heating element has a longitudinal length less than a longitudinal length of the bushing within the elongate conduit.

23. The device of Embodiment 22, wherein the bushing includes an intermediate portion between the first open end and the second open end, and wherein the heating element is configured to radially irradiate the intermediate portion.

24. The device of any one of Embodiments 18-23, wherein the heating element is configured to cauterize a mouth of the diverticulum.

25. The device of Embodiment 16 or 17, wherein the bushing comprises:
   a first electrically conductive track;
   a second electrically conductive track; and
   an ohmic resistor between the first electrically conductive track and the second electrically conductive track.

26. The device of Embodiment 25, wherein the containment device includes a distal end comprising:
   a first contact configured to conduct electrical current to the first electrically conductive track; and
   a second contact configured to conduct electrical current to the second electrically conductive track.

27. The device of Embodiment 26, wherein at least one of the first contact and the second contact comprises a spring contact biased radially inwardly.

28. The device of Embodiment 16 or 17, wherein the bushing comprises a foil layer external to the heat-shrink material.

29. The device of Embodiment 28, wherein the bushing comprises a polymer corrosion barrier external to the foil layer.

30. The device of Embodiment 28 or 29, wherein the containment device includes a distal end comprising a solenoid.

31. The device of any one of Embodiments 16-30, wherein the containment device is configured to invert at least a portion of the diverticulum upon application of negative pressure to the elongate conduit of the containment device.

32. The device of any one of Embodiments 16-31, wherein at least one of the first open end of the bushing and the second open end of the bushing comprises a flared end.

33. The device of any one of Embodiments 16-32, wherein the first open end of the bushing comprises a trumpeted end.

34. The device of any one of Embodiments 16-33, wherein the first open end of the bushing comprises a plurality of longitudinal slots.

35. The device of any one of Embodiments 16-33, wherein the first open end of the bushing comprises a ring not including the heat-shrink material.

36. The device of any one of Embodiments 16-35, wherein the bushing comprises a longitudinal slot between the first open end and the second open end, the longitudinal slot configured such that the bushing folds upon itself upon heating the heat-shrink material.

37. The device of any one of Embodiments 16-36, wherein the bushing comprises a roughened inner surface configured to frictionally engage the inverted diverticulum.

38. The device of any one of Embodiments 16-37, wherein a ratio of a transverse diameter of the bushing to a longitudinal length of the bushing is between about 0.5:1 and about 2:1.

39. The device of any one of Embodiments 16-38, comprising a plurality of said bushings arranged longitudinally in the elongate conduit of the containment device.

40. The device of Embodiment 39, further comprising a pusher configured to longitudinally distally advance the plurality of bushings.

41. The device of any one of Embodiments 16-40, wherein the containment device comprises an imaging system configured to monitor transforming the bushing from the first tubular shape toward the second shape.

42. The device of any one of Embodiments 16-41, wherein the containment device comprises a radially inward protrusion distal to the bushing, the radially inward protrusion configured to inhibit the bushing from exiting the containment device in the first tubular shape.

43. The device of any one of Embodiments 16-42, wherein the containment device comprises an inner surface configured to frictionally inhibit the bushing from exiting the containment device in the first tubular shape.

44. The device of any one of Embodiments 16-43, wherein the containment device comprises a thermally insulated endoscope head configured to inhibit heating of biologic tissue not within the elongate conduit.

45. The device of any one of Embodiments 16-44, wherein a colonoscope comprises the containment device.

46. A bushing for treating a diverticulum, the bushing comprising:
   a first open end;
   a second open end;
   a tubular body between the first open end and the second open end;
   a first electrically conductive track proximate to the first open end;
   a second electrically conductive track proximate to the second open end; and
   an ohmic resistor between the first electrically conductive track and the second electrically conductive track, the tubular body including heat-shrink material configured to compress radially inwardly upon application of an electric current between the first electrically conductive track and the second electrically conductive track.

47. A bushing for treating a diverticulum, the bushing comprising:
   a first open end;
   a second open end; and
   a tubular body between the first open end and the second open end, the tubular body including:
      heat-shrink material; and
      a foil layer external to the heat-shrink material, the heat-shrink material configured to compress radially inwardly upon application of an inductive current to the foil layer.

48. The bushing of Embodiment 47, wherein the tubular body further comprises a polymer barrier external to the foil layer.

49. The bushing of any one of Embodiments 46-48, wherein the heat-shrink material comprises at least one of nylon, thermoplastic such as polyolefin, fluoropolymer, fluorinated ethylene propylene (FEP), polytetrafluoroethylene (PTFE), polyvinylidene fluoride (PVDF), polyvinyl chloride (PVC), polycholorprene, and silicone elastomer.

50. The bushing of any one of Embodiments 46-49, wherein at least one of the first open end and the second open end comprises a flared end.

51. The bushing of any one of Embodiments 46-50, wherein the first open end comprises a trumpeted end.

52. The bushing of any one of Embodiments 46-51, wherein the first open end comprises a plurality of longitudinal slots.

53. The bushing of any one of Embodiments 46-52, comprising a longitudinal slot extending from the first open end to the second open end, the longitudinal slot configured such that the bushing folds upon itself upon heating the heat-shrink material.

54. The bushing of any one of Embodiments 46-53, comprising a plurality of transverse slots between the first open end and the second open end, the plurality of transverse slots configured to increase longitudinal flexibility of the bushing.

55. The bushing of any one of Embodiments 46-54, comprising a spiral cut between the first open end and the second open end, the spiral cut configured to increase longitudinal flexibility of the bushing.

56. A containment device for a bushing for treating a diverticulum, the device comprising:
   an elongate conduit having a distal end; and
   a heater proximate to the distal end of the conduit, the heater configured heat heat-shrink material of a bushing in the distal end of the conduit to change the bushing from a first tubular shape toward a second shape upon heating the heat-shrink material.

57. The device of Embodiment 56, wherein the heater comprises a resistive heating element.

58. The device of Embodiment 57, wherein the resistive heating element comprises a tungsten wire.

59. The device of Embodiment 57 or 58, wherein the resistive heating element comprises a ceramic block.

60. The device of Embodiment 56, wherein the heater comprises:
   a first flexible contact configured to conduct electrical current to a first electrically conductive track of the bushing; and
   a second flexible contact configured to conduct electrical current to a second electrically conductive track of the bushing.

61. The device of Embodiment 60, wherein at least one of the first flexible contact and the second flexible contact comprises a spring contact biased radially inwardly.

62. The device of Embodiment 56, wherein the heater comprises a solenoid.

63. The device of any one of Embodiments 56-62, wherein the heater has a longitudinal length less than a longitudinal length of the bushing.

64. The device of any one of Embodiments 56-63, wherein the heater is configured to cauterize a mouth of the diverticulum.

65. The device of any one of Embodiments 56-64, wherein the device is configured to invert at least a portion of the diverticulum upon application of negative pressure to the elongate conduit of the containment device.

66. The device of any one of Embodiments 56-65, further comprising a pusher configured to longitudinally distally advance a plurality of bushings.

67. The device of any one of Embodiments 56-66, further comprising an imaging system configured to monitor transforming the bushing from the first tubular shape toward the second shape.

68. The device of any one of Embodiments 56-67, further comprising a radially inward protrusion configured to inhibit the bushing from exiting the conduit in the first tubular shape.

69. The device of any one of Embodiments 56-68, further comprising an inner surface configured to frictionally inhibit the bushing from exiting the conduit in the first tubular shape.

70. The device of any one of Embodiments 56-69, further comprising a thermally insulated endoscope head configured to inhibit heating of biologic tissue not within the elongate conduit.

71. A colonoscope comprising the device of any one of Embodiments 56-70.

What is claimed is:

1. A method to treat a diverticulum of a body lumen, the method comprising:
    positioning the diverticulum in an inverted state at least partially into a first open end of a bushing in an elongate conduit of a containment device, wherein the bushing includes a heat-shrink material; and
    transforming the bushing from a first tubular shape toward a second shape, wherein the first tubular shape includes the first open end and a second open end, and the second shape includes at least a portion of the bushing located radially inward relative to the first tubular shape, wherein transforming the bushing includes heating the heat-shrink material, and wherein after transforming the bushing, the bushing in the second shape holds the diverticulum in a radially compressed inverted state.

2. The method of claim 1, wherein the containment device includes a distal end that comprises a resistive heating element and wherein heating the heat-shrink material comprises applying current to the resistive heating element.

3. The method of claim 1, wherein the containment device includes a distal end that comprises flexible electrical contacts and wherein heating the heat-shrink material comprises applying current to the flexible electrical contacts.

4. The method of claim 1, wherein the containment device includes a distal end that comprises a solenoid and wherein heating the heat-shrink material comprises applying current to the solenoid.

5. The method of claim 1, wherein after transforming the bushing, at least part of the diverticulum in the inverted state extends out of the second open end of the bushing.

6. The method of claim 1, further comprising cauterizing a mouth of the diverticulum in the inverted state.

7. The method of claim 1, further comprising applying pressure to the diverticulum sufficient to cause at least a portion of the diverticulum to invert.

8. The method of claim 7, wherein applying the pressure comprises applying negative pressure within the elongate conduit of the containment device.

9. The method of claim 1, further comprising imaging the bushing during transforming the bushing.

10. The method of claim 1, wherein the body lumen is a colon.

11. The method of claim 1, wherein the containment device is in a colonoscope and wherein the method further comprises advancing the colonoscope proximate to the diverticulum.

12. The method of claim 1, further comprising deploying the bushing out of the elongate conduit of the containment device.

13. The method of claim 12, wherein deploying the bushing out of the elongate conduit of the containment device comprises deploying the bushing out of a longitudinal end of the containment device.

14. The method of claim 12, wherein deploying the bushing out of the elongate conduit of the containment device comprises deploying the bushing out of a side of the containment device.

15. The method of claim 1, further comprising, after transforming the bushing and without withdrawing the containment device from the body lumen,
    distally advancing a second bushing in the elongate conduit of the containment device, wherein the second bushing includes a heat-shrink material, a first open end, and a second open end;
    positioning a second diverticulum in an inverted state at least partially into the first open end of the second bushing in the elongate conduit of the containment device; and
    transforming the second bushing from a first tubular shape toward a second shape, wherein the first tubular shape includes the first open end and the second open end, and the second shape includes at least a portion of the second bushing located radially inward relative to the first tubular shape, wherein transforming the second bushing includes heating the heat-shrink material, and wherein after transforming the second bushing, the second bushing in the second shape holds the second diverticulum in a radially compressed inverted state.

16. A device to treat a diverticulum, the device comprising:
    a containment device that includes an elongate conduit, wherein the elongate conduit is a hollow space running inside and along a length of the containment device; and
    a bushing in the elongate conduit of the containment device, wherein the bushing includes a heat-shrink material,
    wherein the bushing has a first tubular shape that includes a first open end and a second open end, at least a portion of the diverticulum in an inverted state positionable into the first open end, the bushing is configured to transform from the first tubular shape toward a second shape upon heating the heat-shrink material, the second shape includes at least a portion of the bushing located radially inward relative to the first tubular shape, and the bushing in the second shape is configured to hold the diverticulum in a radially compressed inverted state.

17. A bushing to treat a diverticulum, the bushing comprising:
    a first open end;
    a second open end;
    a tubular body between the first open end and the second open end;
    a first electrically conductive track proximate to the first open end;
    a second electrically conductive track proximate to the second open end; and an ohmic resistor between the first electrically conductive track and the second electrically conductive track; wherein the tubular body includes a heat-shrink material configured to compress radially inwardly upon application of an electric current between the first electrically conductive track and the second electrically conductive track.

18. A bushing to treat a diverticulum, the bushing comprising:
  a first open end;
  a second open end; and
  a tubular body between the first open end and the second open end, wherein the tubular body includes:
    a heat-shrink material; and
    a foil layer external to the heat-shrink material, wherein the heat-shrink material is configured to compress radially inwardly upon application of an inductive current to the foil layer.

\* \* \* \* \*